US009150606B2

(12) United States Patent
Allerson et al.

(10) Patent No.: US 9,150,606 B2
(45) Date of Patent: Oct. 6, 2015

(54) COMPOSITIONS COMPRISING ALTERNATING 2'-MODIFIED NUCLEOSIDES FOR USE IN GENE MODULATION

(75) Inventors: Charles Allerson, Carlsbad, CA (US); Balkrishen Bhat, Carlsbad, CA (US); Anne B. Eldrup, Danbury, CT (US); Muthiah Manoharan, Weston, MA (US); Richard H. Griffey, Vista, CA (US); Brenda F. Baker, Carlsbad, CA (US); Eric E. Swayze, Carlsbad, CA (US)

(73) Assignee: Isis Pharmaceuticals, Inc., Carlsbad, CA (US)

(*) Notice: Subject to any disclaimer, the term of this patent is extended or adjusted under 35 U.S.C. 154(b) by 147 days.

(21) Appl. No.: 11/054,848

(22) Filed: Feb. 9, 2005

(65) Prior Publication Data

US 2005/0187178 A1  Aug. 25, 2005

Related U.S. Application Data

(63) Continuation-in-part of application No. 10/860,265, filed on Jun. 3, 2004, which is a continuation-in-part of application No. 10/701,007, filed on Nov. 4, 2003, now Pat. No. 8,604,183.

(60) Provisional application No. 60/423,760, filed on Nov. 5, 2002, provisional application No. 60/555,521, filed on Mar. 22, 2004.

(51) Int. Cl.
C07H 21/02 (2006.01)

(52) U.S. Cl.
CPC ...................................... C07H 21/02 (2013.01)

(58) Field of Classification Search
USPC ............ 435/6.1, 91.1, 91.31, 45.5, 4.58, 455, 435/458; 514/44; 536/23.1, 24.3, 24.5
See application file for complete search history.

(56) References Cited

U.S. PATENT DOCUMENTS

| | | |
|---|---|---|
| 3,687,808 A | 8/1972 | Merigan, Jr. et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,668,777 A | 5/1987 | Caruthers et al. |
| 4,725,677 A | 2/1988 | Koster et al. |
| 4,762,779 A | 8/1988 | Snitman et al. |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh et al. |
| 4,876,335 A | 10/1989 | Yamane et al. |
| 4,904,582 A | 2/1990 | Tullis et al. |
| 4,948,882 A | 8/1990 | Ruth et al. |
| 4,958,013 A | 9/1990 | Letsinger et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis et al. |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| 5,138,045 A | 8/1992 | Cook et al. |
| RE34,069 E | 9/1992 | Koster et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,214,136 A | 5/1993 | Lin et al. |
| 2,220,007 A | 6/1993 | Pederson et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren, III et al. |
| 5,256,775 A | 10/1993 | Froehler |

(Continued)

FOREIGN PATENT DOCUMENTS

| | | |
|---|---|---|
| WO | WO 86/05518 | 9/1986 |
| WO | WO 89/12060 | 12/1989 |

(Continued)

OTHER PUBLICATIONS

Elbashir et al., EMBO J., vol. 20, No. 23, pp. 6877-6888 (2001).*

(Continued)

Primary Examiner — Jane Zara
(74) Attorney, Agent, or Firm — Baker Hofstetler

(57) ABSTRACT

The present invention provides compositions comprising at least one oligomeric compound comprising an alternating motif and further include a region that is complementary to a nucleic acid target. The compositions are useful for targeting selected nucleic acid molecules and modulating the expression of one or more genes. In preferred embodiments the compositions of the present invention hybridize to a portion of a target RNA resulting in loss of normal function of the target RNA. The present invention also provides methods for modulating gene expression.

21 Claims, No Drawings

(56) References Cited

U.S. PATENT DOCUMENTS

| | | |
|---|---|---|
| 5,258,506 A | 11/1993 | Urdea et al. |
| 5,262,536 A | 11/1993 | Hobbs, Jr. et al. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,565,555 A | 10/1996 | Froehler et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,607,922 A | 3/1997 | De Clercq et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,312 A | 5/1997 | Kabeta et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,940 A | 10/1997 | Wang et al. |
| 5,681,941 A | 10/1997 | Cook et al. |
| 5,688,941 A | 11/1997 | Cook et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,760,209 A | 6/1998 | Cheruvallath et al. |
| 5,763,588 A | 6/1998 | Matteucci et al. |
| 5,780,607 A | 7/1998 | Goodnow, Jr. et al. |
| 5,792,608 A | 8/1998 | Swaminathan et al. |
| 5,792,747 A | 8/1998 | Schally et al. |
| 5,808,036 A | 9/1998 | Kool |
| 5,830,635 A | 11/1998 | Agnello |
| 5,854,410 A | 12/1998 | Arnold, Jr. et al. |
| 5,874,553 A | 2/1999 | Peyman et al. |
| 5,898,031 A | 4/1999 | Crooke |
| 5,955,443 A | 9/1999 | Bennett et al. |
| 6,005,096 A | 12/1999 | Matteucci et al. |
| 6,033,910 A | 3/2000 | Monia et al. |
| 6,046,306 A | 4/2000 | Breipohl et al. |
| 6,107,094 A | 8/2000 | Crooke |
| 6,127,346 A | 10/2000 | Peyman et al. |
| 6,133,246 A * | 10/2000 | McKay et al. .............. 514/44 A |
| 6,150,510 A | 11/2000 | Seela et al. |
| 6,172,209 B1 | 1/2001 | Manoharan et al. |
| 6,262,036 B1 * | 7/2001 | Arnold et al. ................ 514/44 A |
| 6,271,358 B1 | 8/2001 | Manoharan et al. |
| 6,294,522 B1 | 9/2001 | Zablocki et al. |
| 6,329,346 B1 | 12/2001 | Muhlegger et al. |
| 6,380,169 B1 | 4/2002 | Adams et al. |
| 6,395,474 B1 | 5/2002 | Buchardt et al. |
| 6,426,220 B1 | 7/2002 | Bennett et al. |
| 6,436,640 B1 | 8/2002 | Simmons et al. |
| 6,656,730 B1 | 12/2003 | Manoharan |
| 2002/0068708 A1 | 6/2002 | Wengel et al. |
| 2002/0081736 A1 | 6/2002 | Conroy et al. |
| 2002/0132788 A1 | 9/2002 | Lewis et al. |
| 2002/0160393 A1 | 10/2002 | Symonds et al. |
| 2003/0143732 A1* | 7/2003 | Fosnaugh et al. ............ 435/325 |
| 2003/0175906 A1 | 9/2003 | Manoharan et al. |
| 2003/0206887 A1* | 11/2003 | Morrissey et al. ........... 424/93.2 |
| 2004/0018999 A1 | 1/2004 | Beach et al. |

(56) References Cited

U.S. PATENT DOCUMENTS

| | | | |
|---|---|---|---|
| 2004/0180351 A1* | 9/2004 | Giese et al. | 435/6 |
| 2005/0020525 A1 | 1/2005 | McSwiggen et al. | |
| 2005/0142535 A1* | 6/2005 | Damha et al. | 435/5 |
| 2006/0127891 A1* | 6/2006 | McSwiggen et al. | 435/6 |

FOREIGN PATENT DOCUMENTS

| | | |
|---|---|---|
| WO | WO 93/07883 | 4/1993 |
| WO | WO 94/01550 | 1/1994 |
| WO | WO 94/23026 | 10/1994 |
| WO | WO 95/13834 | 5/1995 |
| WO | WO 97/26270 | 7/1997 |
| WO | WO 99/14226 | 3/1999 |
| WO | WO 99/32619 | 7/1999 |
| WO | WO 00/08044 | 2/2000 |
| WO | WO 00/44895 | 8/2000 |
| WO | WO 00/44914 | 8/2000 |
| WO | WO 00/49035 | 8/2000 |
| WO | WO 00/63364 | 10/2000 |
| WO | WO 01/29058 | 4/2001 |
| WO | WO 01/36641 | 5/2001 |
| WO | WO 01/36646 | 5/2001 |
| WO | WO 01/48183 | 7/2001 |
| WO | WO 01/75164 | 10/2001 |
| WO | WO 02/36743 | 5/2002 |
| WO | WO 02/44321 | 6/2002 |
| WO | WO 03/004602 | 1/2003 |
| WO | WO 03/072705 | 9/2003 |

OTHER PUBLICATIONS

Opalinska, J.B. et al., Nature Rev., vol. 1, pp. 503-514 (2002).*
Chirila, T.V. et al., Biomaterials, vol. 23, pp. 321-342 (2002).*
Peracchi, A., Rev. Med. Virol., vol. 14, pp. 47-64 (2004).*
Elbashir et al., EMBO J.,vol. 20, No. 23, pp. 6877-6888 (2001).*
Agrawal, S. et al., Molecular Med. Today, vol. 6, pp. 72-81 (2000).*
Branch, A.D., Trends, in Biochem. Scil, vol. 23, pp. 45-50 (1998).*
Abe, A. et al., "Conformational Energies and the Random-Coil Dimensions and Dipole Moments of the Polyoxides $CH_3O[(CH_2)_yO]_xCH_3$," J. Am. Chem. Soc. (1976) 98(21):6468-6476.
Agrawal, S. (ed.) Protocols for Oligonucleotides & Analogs (1993), Humana Press, Totowa.
Altmann, K.-H. et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides," Nucleosides Nucleotides (1997) 16(7-9):917-926.
Altmann, K.-H. et al., "Second-generation antisense oligonucleotides: structure-activity relationships and the design of improved signal-transduction inhibitors," Biochem. Soc. Trans. (1996) 24: 630-637.
Altmann, K.-H. et al., "Second Generation of Antisense Oligonucleotides: From Nuclease Resistance to Biological Efficacy in Animals," Chimia (1996) 50: 168-176.
Altschul, S. F. et al., "Basic Local Alignment Search Tool," J. Mol. Biol. (1990) 215: 403-10.
Amarzguioui, M. et al., "Tolerance for mutations and chemical modifiecations in a siRNA," Nucleic Acids Res. (2003) 31(2):589-595.
Baker, B. F. et al., "2'-O-(2'-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells," J. Biol. Chem. (1997) 272(18): 11994-12000.
Bass, B. L., "Double-Stranded RNA as a Template for Gene Silencing," Cell (2000) 101:235-8.
Beaucage, S. L. et al., "The Functionalization of Oligonucleotides Via Phosphoramidite Derivatives," Tetrahedron (1993) 49(10): 1925-1963.
Beigelman, L. et al., "Chemical Modification of Hammerhead Ribozymes," J. Biol. Chem. (1995) 270(43): 25702-25708.

Boutla, A. et al., "Short 5'-phosphorylated double-stranded RNAs induce RNA interference in Drosophila," Curr. Biol. (2001) 11:1776-1780.
Braasch, D. A. et al., "RNA Interference in Mammalian Cells by Chemically-Modified RNA," Biochem. (2003) 42(26): 7967-7975.
Brantl, S., "Antisense-RNA regulation and RNA interference," Biochim. Biophys. Acta (2002) 1575: 15-25.
Caplen, N. J. et al., "Specific inhibition of gene expression by small double-stranded RNAs in invertebrate and vertebrate systems," PNAS (2001) 98(17): 9742-9747.
Chiu, Y.-L. et al., "siRNA function in RNAi: A chemical modification analysis," RNA (2003) 9: 1034-1038.
Cogoni, C. et al., "Post-transcriptional gene silencing across kingdoms," Curr. Opin. Gene. Dev. (2000) 10: 638-643.
Conte, M. R. et al., "Conformational properties and thermodynamics of the RNA duplex r(CGCAAAUUUGCG)$_2$: comparison with the DNA analogue d(CGCAAATTTGCG)$_2$," Nucleic Acids Res. (1997) 25(13): 2627-2634.
Crooke, S. T. et al, "Pharmacokinetic Properties of Several Novel Oligonucleotide Analogs in mice," J. Pharmacol. Exp. Ther. (1996) 277: 923-937.
Czauderna, F. et al., "Structural variations and stabilizing modifications of synthetic siRNAs in mammalian cells," Nucleic Acids Res. (2003)31(11): 2705-2716.
Eckstein, F. (ed.) Oligonucleotides and Analogues: A Practical Approach (1991), IRL Press, Oxford.
Egli, M. et al., "RNA Hydration: A Detailed Look," Biochem. (1996) 35(26):8489-8494.
Elbashir, S. M. et al., "Functional anatomy of siRNAs for mediating efficient RNAi in Drosophila melanogaster embryo lysate," EMBO J. (2001) 20(23):6877-6888.
Elbashir, S. M. et al., "RNA interference is mediated by 21- and 22-nucleotide RNAs," Genes Dev. (2001) 15:188-200.
Elbashir, S. M. et al., "Duplexes of 21-nucleotide RNAs mediate RNA interference in cultured mammalian cells," Nature (2001) 411: 494-498.
Englisch, U. et al., "Chemically Modified Oligonucleotides as Probes and Inhibitors," Ange. Chemie. (1991) 30(6): 613-722.
Fedoroff, O. Y. et al., "Structure of a DNA:RNA Hybrid Duplex," J. Mol.Biol.(1993) 233: 509-523.
Fire, A. et al., "Potent and specific genetic interference by double-stranded RNA in Caenorhabditis elegans," Nature (1998) 391: 806-811.
Francis, A. W. et al., "Probing the Requirements for Recognition and Catalysis in Fpg and MutY with Nonpolar Adenine Isosteres,"J. Am. Chem. Soc. (2003) 125(52): 16235-16242.
Fraser, A. et al., "Synthesis and Conformational Properties of 2'-Deoxy-2'methylthio-pyrimidine and—purine Nucleosides: Potential Antisense Applications," J. Heterocyclic Chem. (1993) 30; 1277-1287.
Freier, S. M. et al., "The ups and downs of nucleic acid duplex stability: structure-stability studies on chemically-modified DNA:RNA duplexes," Nucleic Acids Res. (1997) 25(22):4429-4443.
Gait, M. J., "Oligoribonucleotides," Antisense Research and Applications (1993) Crooke, S. T. and Lebleu, B. (eds.), CRC Press, Inc., Boca Raton, pp. 289-301.
Gallo, M. et al., "2'-C-Methyluridine phosphoramidite: a new building block for the preparation of RNA analogues carrying the 2'-hydroxyl group," Tetrahedron (2001) 57: 5707-13.
Gao, J. et al., "Expanded-Size Bases in Naturally Sized DNA: Evaluation of Steric Effects in Watson-Crick Pairing," J. Am. Chem. Soc. (2004) 126(38): 11826-11831.
Gonzalez, C. et al., "Structure and Dynamics of a DNA•RNA Hybrid Duplex with a Chiral Phosphorothioate Moiety: NMR and Molecular Dynamics with Conventional and Time-Averaged Restraints," Biochem. (1995) 34(15): 4969-4982.
Gravert, D. J. et al., "Organic Synthesis on Soluble Polymer Supports: Liquid-Phase Methodologies," Chem. Rev. (1997) 97(2): 489-509.
Greene, T. et al., Protective Groups in Organic Synthesis (1991) 3$^{rd}$ ed:, John Wiley & Sons, New York.

(56) References Cited

OTHER PUBLICATIONS

Guckian, K. M. et al., "Structure and Base Pairing Properties of a Replicable Nonpolar Isostere for Deoxyadenosine," *J. Org. Chem.* (1998) 63(26): 9652-9656.

Guo, S. et al., "*par*-1, a Gene Required for Establishing Polarity in C. elegans Embryos, Encodes a Putative Ser/Thr Kinase That Is Asymmetrically Distributed," *Cell* (1995) 81: 611-620.

Gura, T., "A silence that speaks volumes," *Nature* (2000) 404: 804-808.

Hill, F. et al., "Polymerase recognition of synthetic oligodeoxyribonucleotides incorporating degenerate pyrimidine and purine bases," *Proc. Natl. Acad. Sci. USA* (1998) 95: 4258-4263.

Holen, T. et al., "Similar behaviour of single-strand and double-strand siRNAs suggests they act through a common RNAi pathway," *Nucleic Acids Res.* (2003) 31(9): 2401-2407.

Horton, N. C. et al., "The Structure of an RNA/DNA Hybrid: A Substrate of the Ribonuclease Activity of HIV-1 Reverse Transcriptase," *J. Mol. Biol.* (1996) 264: 521-533.

Jorgensen, R. A. et al., "Chalcone synthase cosuppression phenotypes in petunia flowers: comparison of sense vs. antisense constructs and single-copy vs. complex T-DNA sequences," *Plant Mol. Biol.* (1996) 32: 957-973.

Kabanov, A. V. et al., "A new class of antivirals: antisense oligonucleotides combined with a hydrophobic substituent effectively inhibit influenza virus reproduction and synthesis of virus-specific proteins in MDCK cells," *FEBS Lett.* (1990) 259(2): 327-330.

Klöpffer, A. E. et al., "Synthesis of 2'-Aminoalkyl-Substitued Fluorinated Nucleobases and Their Influence on the Kinetic Properties of Hammerhead Ribozymes," *ChemBioChem* (2004) 5: 707-716.

Klöpffer, A. E. et al., "The Effect of Universal Fluorinated Nucleobases on the Catalytic Activity of Ribozymes," *Nucleosides Nucleotides Nucleic Acids* (2003) 22(5-8): 1347-1350.

Kroschwitz, J. I. (ed.), "Polynucleotides," *Concise Encyclopedia of Polymer Science and Engineering* (1990) John Wiley & Sons, New York, pp. 858-859.

Kurchavov, N. A. et al., "A New Phosphoramidite Reagent for the Incorporation of Diazaphenoxazinone Nucleoside with Enhanced Base-Pairing Properties into Oligodeoxynucleotides," *Nucleosides Nucleotides* (1997) 16(10&11): 1837-1846.

Lai, J. S. et al., "Selective Pairing of Polyfluorinated DNA Bases," *J. Am. Chem. Soc.* (2004) 126(10): 3040-3041.

Lai, J. S. et al., "Fluorinated DNA Bases as Probes of Electrostatic Effects in DNA Base Stacking," *Angew. Chem. Int. Ed.* (2003) 42: 5973-5977.

Lane, A. N. et al., "NMR assignments and solution conformation of the DNA•RNA hybrid duplex d(GTGAACTI)•r(AAGUUCAC)," *Eur. J. Biochem.* (1993) 215: 297-306.

Lesnik, E. A. et al., "Relative Thermodynamic Stability of DNA, RNA, and DNA:RNA Hybrid Duplexes: Relationship with Base Composition and Structure," *Biochem.* (1995) 34(34):1080710815.

Letsinger, R. L. et al., "Cholesteryl-conjugated oligonucleotides: Synthesis, properties, and activity as inhibitors of replication of human immunodeficiency virus in cell culture," *Proc. Natl. Acad. Sci. USA* (1989) 86: 6553-6556.

Limbach, P. A. et al., "Summary: the modified nucleosides of RNA," *Nucleic Acids Res.* (1994) 22(12): 2183-2196.

Lin, K.-Y. et al., "Tricyclic 2'-Deoxycytidine Analogs: Syntheses and Incorporation into Oligodeoxynucleotides Which Have Enhanced Binding to Complementary RNA," *J. Am. Chem. Soc.* (1995) 117(13): 3873-3874.

Lipardi, C. et al., "RNAi as Random Degradative PCR: siRNA Primers Convert mRNA into dsRNAs that are Degraded to Generate New siRNAs," *Cell* (2001) 107: 297-307.

Liu, H. et al., "A Four-Base Paired Genetic Helix with Expanded Size," *Science* (2003) 302: 868-871.

Liu, H. et al., "Toward a New Genetic System with Expanded Dimensions: Size-Expanded Analogues of Deoxyadenosine and Thymidine," *J. Am. Chem. Soc.* (2004) 126(4): 1102-1109.

Loakes, D., "The applications of universal DNA base analogues," *Nucleic Acids Res.* (2001) 29(12): 2437-2447.

Manoharan, M. et al., "Introduction of a Lipophilic Thioether Tether in the Minor Groove of Nucleic Acids for Antisense Applications," *Bioorg. Med. Chem. Lett.* (1993) 3(12): 2765-2770.

Manoharan, M. et al., "Cholic Acid-Oligonucleotide Conjugates for Antisense Applications," *Bioorg. Med. Chem. Lett.* (1994) 4(8): 1053-1060.

Manoharan, M. et al., "Oligonucleotide Conjugates: Alteration of the Pharmacokinetic Properties of Antisense Agents," *Nucleosides Nucleotides* (1995) 14(3-5): 969-973.

Manoharan, M. et al., "Lipidic Nucleic Acids," *Tetrahedron Letters* (1995) 36(21): 3651-4.

Manoharan, M. et al., "Chemical Modifications to Improve Uptake and Bioavailability of Antisense Oligonucleotides," *Ann. N.Y. Acad. Sci.* (1992) 660: 306-309.

Martin, P., "Ein neuer Zugang zu 2'-O-Alkylribonucleosiden and Eigenschaften deren Oligonucleotide," *Helv. Chim. Acta* (1995) 78: 486-504.

Martinez, J. et al., " Single-Stranded Antisense siRNAs Guide Target RNA Cleavage in RNAi," *Cell* (2002) 110: 563-574.

Mellitzer, G. et al., "Spatial and temporal 'knock down' of gene expression by electroporation of double-stranded RNA and morpholinos into early postimplantation mouse embryos," *Mech. Dev.* (2002) 118: 57-63.

Mishra, R. K. et al., "Improved leishmanicidal effect of phosphorothioate antisense oligonucleotides by LDL-mediated delivery," *Biochim. Biophys. Acta* (1995) 1264: 229-237.

Montgomery, M. K. et al., "RNA as a target of double-stranded RNA-mediated genetic interference in Caenorhabditis elegans," *Proc. Natl. Acad. Sci. USA* (1998) 95: 15502-15507.

Moran, S. et al., "Difluorotoluene, a Nonpolar Isostere for Thymine, Codes Specifically and Efficiently for Adenine in DNA Replication," *J. Am. Chem. Soc.* (1997) 119(8): 2056-7.

Moran, S. et al., "A thymidine triphosphate shape analog lacking Watson-Crick pairing ability is replicated with high sequence selectivity," *Proc. Natl. Acad. Sci. USA* (1997) 94: 10506-11.

Napoli, C. et al, "Introduction of a Chimeric Chalcone Synthase Gene into Petunia Results in Reversible Co-Suppression of Homologous Genes in trans," *Plant Cell*(1990) 2: 279-289.

Nishikura, K., "A Short Primer on RNAi: Rna-Directed Rna Polymerase Acts as a Key Catalyst," *Cell* (2001) 107: 415-418.

Oberhauser, B. et al., "Effective incorporation of 2'-O-methyl-oligoribonucleotides into liposomes and enhanced cell association through modification with thiocholesterol," *Nucleic Acids Res.* (1992) 20(3): 533-538.

O'Neill, B. M. et al., "A Highly Effective Nonpolar Isostere of Deoxyguanosine: Synthesis, Structure, Stacking, and Base Pairing," *J. Org. Chem.* (2002) 67(17): 5869-5875.

Paddison, P. J. et al., "Stable suppression of gene expression by RNAi in mammalian cells," *PNAS* (2002) 99(3): 1443-1448.

Parrish, S. et al., "Functional Anatomy of a dsRNA Trigger: Differential Requirement for the Two Trigger Strands in RNA Interference," *Mol. Cell.* (2000)6: 1077-1087.

Rajwanshi, V. K. et al., "LNA stereoisomers: *xylo*-LNA (β-D-*xylo* configured locked nucleic acid) and α-L-LNA (α-L-ribo configured locked nucleic acid)," *Chem. Commun.* (1999):1395-6.

Rausch, J. W. et al., "Hydrolysis of RNA/DNA hybrids containing nonpolar pyrimidine isosteres defines regions essential for HIV type 1 polypurine tract selection," *PNAS* (2003) 100(20): 11279-11284.

Saison-Behmoaras, T. et al., "Short modified antisense oligonucleotides directed against Ha-ras point mutation induce selective cleavage of the mRNA and inhibit T24 cells proliferation," *EMBO J.* (1991) 10(5): 1111-1118.

Saenger, W., *Principles of Nucleic Acid Structure* (1984) Springer Verlag, New York.

Sanghvi, Y. S., "Heterocyclic Base Modifications in Nucleic Acids and Their Applications in Antisense Oligonucleotides," *Antisense Research and Applications* (1993) Crooke, S. T. And Lebleu, B. (eds.), CRC Press, Boca Raton, pp. 273-288.

Scaringe, S. A., "RNA Oligonucleotide Synthesis via 5'-Sily1-2'-Orthoester Chemistry," *Methods* (2001) 23: 206-217.

(56) References Cited

OTHER PUBLICATIONS

Schwarz, D. S. et al., "Evidence that siRNAs Function as Guides, Not Primers, in the *Drosophila* and Human RNAi Pathways," *Mol. Cell.* (2002) 10: 537-548.

Searle, M. S. et al., "On the stability of nucleic acid structures in solution: enthalpy—entropy compensations, internal rotations and reversibility," *Nucleic Acids Res.* (1993) 21(9): 2051-6.

Shea, R. G. et al., "Synthesis, hybridization properties and antiviral activity of lipid-oligodeoxynucleotide conjugates," *Nucleic Acids Res.* (1990) 18(13): 3777-3783.

Steffens, R. et al., "Synthesis and Thermodynamic and Biophysical Properties of Tricyclo-DNA," *J. Am. Chem. Soc.* (1999) 121(14): 3249-3255.

Sui, G. et al., "A DNA vector-based RNAi technology to suppress gene expression in mammalian cells," *PNAS* (2002) 99(8): 5515-5520.

Svinarchuk, F. P. et al., "Inhibition of Hiv proliferation in Mt-4 cells by antisense oligonucleotide conjugated to lipophilic groups," Biochimie (1993) 75: 49-54.

Mf Tabara, H. et al.,k "RNAI in C. elegans: Soaking in the Genome Sequence," *Science* (1998) 282:430-431.

Tijsterman, M. et al., "RNA Helicase MUT-14-Dependent Gene Silenxing Triggered in *C. elegans* by Short Antisense RNAs," *Science* (2002) 295: 694-697.

Timmons, L. et al., "Ingestion of bacterially expressed dsRNAs can produce specific and potent genetic interference in *Caenorhabditis elegans*," *Gene* (2001) 263: 103-112.

Timmons, L. et al., "Specific interference by ingested dsRNA," *Nature* (1998) 395: 854.

Tuschl, T. et al., "Targeted mRNA degradation by double-stranded Rna in vitro," *Genes Dev.* (1999) 13: 3191-3197.

Wang, J. et al., "Cyclohexene Nucleic Acids (CeNA): Serum Stable Oligonucleotides that Activate RNase H and Increase Duplex Stability with Complementary RNA," *J. Am. Chem. Soc.* (2000) 122(36): 8595-8602.

Wang, J. et al.,."Synthesis and binding property of an oligonucleotide containing tetrafluorophenoxazine," *Tetrahedron Lett.* (1998) 39: 8385-8388.

Wolfe, S., "The Gauche Effect. Some Stereochemical Consequences of Adjacent Electron Pairs and Polar Bonds," *Acc. Chem. Res.* (1972) 5: 102-111.

Yu, J.-Y. et al., "RNA interference by expression of short-interfering RNAs and hairpin RNAs in mammalian cells," *PNAS* (2002) 99(9): 6047-6052.

Zhang, J. et al., "PowerBLAST: A New Network BLAST Application for Interactive or Automated Sequence Analysis and Annotation," *Genome Res.* (1997) 7: 649-656.

Zhou, Y. et al., "Post-transcriptional suppression of gene expression in *Xenopus embryos* by small interfering RNA," *Nucleic Acids Res.* (2002) 30(7): 1664-1669.

Hunziker, J. et al., "Nucleic Acid Analogues: Synthesis and Properties," *Modern Synthetic Methods* (1995) 331: 333-417.

Leydier, C. et al., "4'-Thio-RNA: Synthesis of Mixed Base 4'-Thio-Oligoribonucleotides, Nuclease Resistance, and Base Pairing Properties with Complementary Single and Double Strand," Antisense Research and Development, 1995, 5, 167-174.

Duroux et al., "Rational design of point mutation-selective antisense DNA targeted to codon 12 of Ha-ras mRNA in human cells" Nucleic Acids Research (1995) 23(17):3411-3418.

Giles et al., "Increased specificity for antisense oligodeoxynucleotide targeting of RNA cleavage of Rnase H using chimeric methylphosphonodiester/phosphodiester structures" Nucleic Acids Research (1992) 20(4):763-770.

\* cited by examiner

SEQUENCE LISTING

<160> NUMBER OF SEQ ID NOS: 25

<210> SEQ ID NO 1
<211> LENGTH: 19
<212> TYPE: DNA
<213> ORGANISM: Artificial Sequence
<220> FEATURE:
<223> OTHER INFORMATION: Antisense Compound

<400> SEQUENCE: 1
cgagaggcgg acgggaccg                                          19

<210> SEQ ID NO 2
<211> LENGTH: 21
<212> TYPE: DNA
<213> ORGANISM: Artificial Sequence
<220> FEATURE:
<223> OTHER INFORMATION: Antisense Compound

<400> SEQUENCE: 2
cgagaggcgg acgggaccgt t                                       21

<210> SEQ ID NO 3
<211> LENGTH: 21

```
<212> TYPE: DNA
<213> ORGANISM: Artificial Sequence
<220> FEATURE:
<223> OTHER INFORMATION: Antisense Compound

<400> SEQUENCE: 3
ttgctctccg cctgccctgg c                                              21

<210> SEQ ID NO 4
<211> LENGTH: 20
<212> TYPE: DNA
<213> ORGANISM: Artificial Sequence
<220> FEATURE:
<223> OTHER INFORMATION: Antisense Compound

<400> SEQUENCE: 4
tccgtcatcg ctcctcaggg                                                20

<210> SEQ ID NO 5
<211> LENGTH: 20
<212> TYPE: DNA
<213> ORGANISM: Artificial Sequence
<220> FEATURE:
<223> OTHER INFORMATION: Antisense Compound

<400> SEQUENCE: 5
gtgcgcgcga gcccgaaatc                                                20

<210> SEQ ID NO 6
<211> LENGTH: 20
<212> TYPE: DNA
<213> ORGANISM: Artificial Sequence
<220> FEATURE:
<223> OTHER INFORMATION: Antisense Compound

<400> SEQUENCE: 6
atgcattctg cccccaagga                                                20

<210> SEQ ID NO 7
<211> LENGTH: 19
<212> TYPE: DNA
<213> ORGANISM: Artificial Sequence
<220> FEATURE:
<223> OTHER INFORMATION: Antisense Compound

<400> SEQUENCE: 7
gctctccgcc tgccctggc                                                 19

<210> SEQ ID NO 8
<211> LENGTH: 20
<212> TYPE: DNA
<213> ORGANISM: Artificial Sequence
<220> FEATURE:
<223> OTHER INFORMATION: Antisense Compound

<400> SEQUENCE: 8
aaguaaggac cagagacaaa                                                20

<210> SEQ ID NO 9
<211> LENGTH: 20
<212> TYPE: DNA
<213> ORGANISM: Artificial Sequence
<220> FEATURE:
<223> OTHER INFORMATION: Antisense Compound

<400> SEQUENCE: 9
```

```
uucauuccug gucucuguuu                                            20

<210> SEQ ID NO 10
<211> LENGTH: 20
<212> TYPE: DNA
<213> ORGANISM: Artificial Sequence
<220> FEATURE:
<223> OTHER INFORMATION: Antisense Compound

<400> SEQUENCE: 10
uuugucucug guccuuacuu                                            20

<210> SEQ ID NO 11
<211> LENGTH: 19
<212> TYPE: DNA
<213> ORGANISM: Artificial Sequence
<220> FEATURE:
<223> OTHER INFORMATION: Antisense Compound

<400> SEQUENCE: 11
ggguaaauac auucuacau                                             19

<210> SEQ ID NO 12
<211> LENGTH: 19
<212> TYPE: DNA
<213> ORGANISM: Artificial Sequence
<220> FEATURE:
<223> OTHER INFORMATION: Antisense Compound

<400> SEQUENCE: 12
auguagaaug uauuuaccc                                             19

<210> SEQ ID NO 13
<211> LENGTH: 19
<212> TYPE: DNA
<213> ORGANISM: Artificial Sequence
<220> FEATURE:
<223> OTHER INFORMATION: Antisense Compound

<400> SEQUENCE: 13
uugucucugg uccuuacuu                                             19

<210> SEQ ID NO 14
<211> LENGTH: 19
<212> TYPE: DNA
<213> ORGANISM: Artificial Sequence
<220> FEATURE:
<223> OTHER INFORMATION: Antisense Compound

<400> SEQUENCE: 14
aaguaaggac cagagacaa                                             19

<210> SEQ ID NO 15
<211> LENGTH: 19
<212> TYPE: DNA
<213> ORGANISM: Artificial Sequence
<220> FEATURE:
<223> OTHER INFORMATION: Antisense Compound

<400> SEQUENCE: 15
ugucauauuc cuggauccu                                             19

<210> SEQ ID NO 16
<211> LENGTH: 19
<212> TYPE: DNA
<213> ORGANISM: Artificial Sequence
```

```
<220> FEATURE:
<223> OTHER INFORMATION: Antisense Compound

<400> SEQUENCE: 16
aggauccagg aauaugaca                                                   19

<210> SEQ ID NO 17
<211> LENGTH: 19
<212> TYPE: DNA
<213> ORGANISM: Artificial Sequence
<220> FEATURE:
<223> OTHER INFORMATION: Antisense Compound

<400> SEQUENCE: 17
uccuggaucc uucaccaau                                                   19

<210> SEQ ID NO 18
<211> LENGTH: 19
<212> TYPE: DNA
<213> ORGANISM: Artificial Sequence
<220> FEATURE:
<223> OTHER INFORMATION: Antisense Compound

<400> SEQUENCE: 18
auuggugaag gauccagga                                                   19

<210> SEQ ID NO 19
<211> LENGTH: 19
<212> TYPE: DNA
<213> ORGANISM: Artificial Sequence
<220> FEATURE:
<223> OTHER INFORMATION: Antisense Compound

<400> SEQUENCE: 19
ucuuaucacc uuuagcucu                                                   19

<210> SEQ ID NO 20
<211> LENGTH: 19
<212> TYPE: DNA
<213> ORGANISM: Artificial Sequence
<220> FEATURE:
<223> OTHER INFORMATION: Antisense Compound

<400> SEQUENCE: 20
agagcuaaag gugauaaga                                                   19

<210> SEQ ID NO 21
<211> LENGTH: 19
<212> TYPE: DNA
<213> ORGANISM: Artificial Sequence
<220> FEATURE:
<223> OTHER INFORMATION: Antisense Compound

<400> SEQUENCE: 21
auacucagaa ggugucuuc                                                   19

<210> SEQ ID NO 22
<211> LENGTH: 19
<212> TYPE: DNA
<213> ORGANISM: Artificial Sequence
<220> FEATURE:
<223> OTHER INFORMATION: Antisense Compound

<400> SEQUENCE: 22
gaagacaccu ucugaguau                                                   19
```

```
<210> SEQ ID NO 23
<211> LENGTH: 19
<212> TYPE: DNA
<213> ORGANISM: Artificial Sequence
<220> FEATURE:
<223> OTHER INFORMATION: Antisense Compound

<400> SEQUENCE: 23
uuugaaaaug uugaucucc                                                  19

<210> SEQ ID NO 24
<211> LENGTH: 19
<212> TYPE: DNA
<213> ORGANISM: Artificial Sequence
<220> FEATURE:
<223> OTHER INFORMATION: Antisense Compound

<400> SEQUENCE: 24
ggagaucaac auuuucaaa                                                  19

<210> SEQ ID NO 25
<211> LENGTH: 20
<212> TYPE: DNA
<213> ORGANISM: Artificial Sequence
<220> FEATURE:
<223> OTHER INFORMATION: Antisense Compound

<400> SEQUENCE: 25
ctgctagcct ctggatttga                                                 20
```

COMPOSITIONS COMPRISING ALTERNATING 2'-MODIFIED NUCLEOSIDES FOR USE IN GENE MODULATION

CROSS REFERENCE TO RELATED APPLICATIONS

The present application is a continuation in part of U.S. application Ser. No. 10/860,265, filed Jun. 3, 2004, which is a continuation in part of U.S. application Ser. No. 10/701,007, filed Nov. 4, 2003, which claims benefit to U.S. Provisional Application Ser. No. 60/423,760 filed Nov. 5, 2002 and Ser. No. 60/555,521, filed Mar. 22, 2004. Each of these applications is incorporated herein in its entirety.

FIELD OF THE INVENTION

The present invention provides modified oligomeric compounds and compositions comprising such modified oligomeric compounds that modulate gene expression. In a preferred embodiment such modulation is via the RNA interference pathway. The modified oligomeric compounds of the invention include alternating motifs that can enhance various physical properties and attributes compared to wild type nucleic acids. The modified oligomeric compounds are used alone or in compositions to modulate targeted nucleic acids. The compositions are useful for targeting selected nucleic acid molecules and modulating the expression of one or more genes. In preferred embodiments the compositions of the present invention hybridize to a portion of a target RNA resulting in loss of normal function of the target RNA.

BACKGROUND OF THE INVENTION

In many species, introduction of double-stranded RNA (dsRNA) induces potent and specific gene silencing. This phenomenon occurs in both plants and animals and has roles in viral defense and transposon silencing mechanisms. This phenomenon was originally described more than a decade ago by researchers working with the petunia flower. While trying to deepen the purple color of these flowers, Jorgensen et al. introduced a pigment-producing gene under the control of a powerful promoter. Instead of the expected deep purple color, many of the flowers appeared variegated or even white. Jorgensen named the observed phenomenon "cosuppression", since the expression of both the introduced gene and the homologous endogenous gene was suppressed (Napoli et al., *Plant Cell,* 1990, 2, 279-289; Jorgensen et al., *Plant Mol. Biol.,* 1996, 31, 957-973).

Cosuppression has since been found to occur in many species of plants, fungi, and has been particularly well characterized in Neurospora crassa, where it is known as "quelling" (Cogoni and Macino, *Genes Dev.* 2000, 10, 638-643; Guru, *Nature,* 2000, 404, 804-808).

The first evidence that dsRNA could lead to gene silencing in animals came from work in the nematode, *Caenorhabditis elegans*. In 1995, researchers Guo and Kemphues were attempting to use antisense RNA to shut down expression of the par-1 gene in order to assess its function. As expected, injection of the antisense RNA disrupted expression of par-1, but quizzically, injection of the sense-strand control also disrupted expression (Guo and Kemphues, *Cell,* 1995, 81, 611-620). This result was a puzzle until Fire et al. injected dsRNA (a mixture of both sense and antisense strands) into *C. elegans*. This injection resulted in much more efficient silencing than injection of either the sense or the antisense strands alone. Injection of just a few molecules of dsRNA per cell was sufficient to completely silence the homologous gene's expression. Furthermore, injection of dsRNA into the gut of the worm caused gene silencing not only throughout the worm, but also in first generation offspring (Fire et al., *Nature,* 1998, 391, 806-811).

The potency of this phenomenon led Timmons and Fire to explore the limits of the dsRNA effects by feeding nematodes bacteria that had been engineered to express dsRNA homologous to the *C. elegans* unc-22 gene. Surprisingly, these worms developed an unc-22 null-like phenotype (Timmons and Fire, *Nature* 1998, 395, 854; Timmons et al., *Gene,* 2001, 263, 103-112). Further work showed that soaking worms in dsRNA was also able to induce silencing (Tabara et al., *Science,* 1998, 282, 430-431). PCT publication WO 01/48183 discloses methods of inhibiting expression of a target gene in a nematode worm involving feeding to the worm a food organism which is capable of producing a double-stranded RNA structure having a nucleotide sequence substantially identical to a portion of the target gene following ingestion of the food organism by the nematode, or by introducing a DNA capable of producing the double-stranded RNA structure (Bogaert et al., 2001).

The posttranscriptional gene silencing defined in *Caenorhabditis elegans* resulting from exposure to double-stranded RNA (dsRNA) has since been designated as RNA interference (RNAi). This term has come to generalize all forms of gene silencing involving dsRNA leading to the sequence-specific reduction of endogenous targeted mRNA levels; unlike co-suppression, in which transgenic DNA leads to silencing of both the transgene and the endogenous gene.

Introduction of exogenous double-stranded RNA (dsRNA) into *Caenorhabditis elegans* has been shown to specifically and potently disrupt the activity of genes containing homologous sequences. Montgomery et al. suggests that the primary interference effects of dsRNA are post-transcriptional; this conclusion being derived from examination of the primary DNA sequence after dsRNA-mediated interference a finding of no evidence of alterations followed by studies involving alteration of an upstream operon having no effect on the activity of its downstream gene. These results argue against an effect on initiation or elongation of transcription. Finally they observed by in situ hybridization, that dsRNA-mediated interference produced a substantial, although not complete, reduction in accumulation of nascent transcripts in the nucleus, while cytoplasmic accumulation of transcripts was virtually eliminated. These results indicate that the endogenous mRNA is the primary target for interference and suggest a mechanism that degrades the targeted MRNA before translation can occur. It was also found that this mechanism is not dependent on the SMG system, an mRNA surveillance system in *C. elegans* responsible for targeting and destroying aberrant messages. The authors further suggest a model of how dsRNA might function as a catalytic mechanism to target homologous mRNAs for degradation. (Montgomery et al., *Proc. Natl. Acad. Sci. USA,* 1998, 95, 15502-15507).

The development of a cell-free system from syncytial blastoderm Drosophila embryos that recapitulates many of the features of RNAi has been reported. The interference observed in this reaction is sequence specific, is promoted by dsRNA but not single-stranded RNA, functions by specific mRNA degradation, and requires a minimum length of dsRNA. Furthermore, preincubation of dsRNA potentiates its activity demonstrating that RNAi can be mediated by sequence-specific processes in soluble reactions (Tuschl et al., *Genes Dev.,* 1999, 13, 3191-3197).

In subsequent experiments, Tuschl et al, using the Drosophila in vitro system, demonstrated that 21- and 22-nt RNA fragments are the sequence-specific mediators of RNAi. These fragments, which they termed short interfering RNAs (siRNAs) were shown to be generated by an RNase III-like processing reaction from long dsRNA. They also showed that chemically synthesized siRNA duplexes with overhanging 3' ends mediate efficient target RNA cleavage in the Drosophila lysate, and that the cleavage site is located near the center of the region spanned by the guiding siRNA. In addition, they suggest that the direction of dsRNA processing determines whether sense or antisense target RNA can be cleaved by the siRNA-protein complex (Elbashir et al., *Genes Dev.*, 2001, 15, 188-200). Further characterization of the suppression of expression of endogenous and heterologous genes caused by the 21-23 nucleotide siRNAs have been investigated in several mammalian cell lines, including human embryonic kidney (293) and HeLa cells (Elbashir et al., *Nature*, 2001, 411, 494-498).

Tijsterman et al. have shown that, in fact, single-stranded RNA oligomers of antisense polarity can be potent inducers of gene silencing. As is the case for co-suppression, they showed that antisense RNAs act independently of the RNAi genes rde-1 and rde4 but require the mutator/RNAi gene mut-7 and a putative DEAD box RNA helicase, mut-14. According to the authors, their data favor the hypothesis that gene silencing is accomplished by RNA primer extension using the mRNA as template, leading to dsRNA that is subsequently degraded suggesting that single-stranded RNA oligomers are ultimately responsible for the RNAi phenomenon (Tijsterman et al., *Science*, 2002, 295, 694-697).

Several other publications have described the structural requirements for the dsRNA trigger required for RNAi activity. Recent reports have indicated that ideal dsRNA sequences are 21nt in length containing 2 nt 3'-end overhangs (Elbashir et al, EMBO (2001), 20, 6877-6887, Sabine Brantl, *Biochimica et Biophysica Acta*, 2002, 1575, 15-25.) In this system, substitution of the 4 nucleosides from the 3'-end with 2'-deoxynucleosides has been demonstrated to not affect activity. On the other hand, substitution with 2'-deoxynucleosides or 2'-OMe-nucleosides throughout the sequence (sense or antisense) was shown to be deleterious to RNAi activity.

Investigation of the structural requirements for RNA silencing in *C. elegans* has demonstrated modification of the internucleotide linkage (phosphorothioate) to not interfere with activity (Parrish et al., *Molecular Cell*, 2000, 6, 1077-1087.) It was also shown by Parrish et al., that chemical modification like 2'-amino or 5'-iodouridine are well tolerated in the sense strand but not the antisense strand of the dsRNA suggesting differing roles for the 2 strands in RNAi. Base modification such as guanine to inosine (where one hydrogen bond is lost) has been demonstrated to decrease RNAi activity independently of the position of the modification (sense or antisense). Same "position independent" loss of activity has been observed following the introduction of mismatches in the dsRNA trigger. Some types of modifications, for example introduction of sterically demanding bases such as 5-iodoU, have been shown to be deleterious to RNAi activity when positioned in the antisense strand, whereas modifications positioned in the sense strand were shown to be less detrimental to RNAi activity. As was the case for the 21 nt dsRNA sequences, RNA-DNA heteroduplexes did not serve as triggers for RNAi. However, dsRNA containing 2'-F-2'-deoxynucleosides appeared to be efficient in triggering RNAi response independent of the position (sense or antisense) of the 2'-F-2'-deoxynucleosides.

In one experiment the reduction of gene expression was studied using electroporated dsRNA and a 25 mer morpholino in post implantation mouse embryos (Mellitzer et al., *Mehanisms of Development*, 2002, 118, 57-63). The morpholino oligomer did show activity but was not as effective as the dsRNA.

A number of PCT applications have been published that relate to the RNAi phenomenon. These include: PCT publication WO 00/44895; PCT publication WO 00/49035; PCT publication WO 00/63364; PCT publication WO 01/36641; PCT publication WO 01/36646; PCT publication WO 99/32619; PCT publication WO 00/44914; PCT publication WO 01/29058; and PCT publication WO 01/75164.

U.S. Pat. Nos. 5,898,031 and 6,107,094, each of which is commonly owned with this application and each of which is herein incorporated by reference, describe certain oligonucleotide having RNA like properties. When hybridized with RNA, these olibonucleotides serve as substrates for a dsRNase enzyme with resultant cleavage of the RNA by the enzyme.

In another published paper (Martinez et al., *Cell*, 2002, 110, 563-574) it was shown that double stranded as well as single stranded siRNA resides in the RNA-induced silencing complex (RISC) together with eIF2C1 and eIf2C2 (human GERp950 Argonaute proteins. The activity of 5'-phosphorylated single stranded siRNA was comparable to the double stranded siRNA in the system studied. In a related study, the inclusion of a 5'-phosphate moiety was shown to enhance activity of siRNA's in vivo in Drosophilia embryos (Boutla, et al., Curr. Biol., 2001, 11, 1776-1780). In another study, it was reported that the 5'-phosphate was required for siRNA function in human HeLa cells (Schwarz et al., *Molecular Cell*, 2002, 10, 537-548).

One group of researchers looked at single strand asRNA and double strand siRNA having 2'-O-methyl groups at select positions (Amarzguioui et al., *Nucleic Acids Research*, 2003, 31(2), 589-595). They compared single strand asRNA wild type with 2'-O—$CH_3$ containing asRNA and showed that the 2'-O-methyl asRNA's showed good activity dependent on the positioning of the modifications but less than wild type. When they put 2'-O-methyl modified nucleosides into siRNA's they showed that these modifications were tolerated in smaller numbers and that there was a loss of activity with increased numbers in wings. They also showed that siRNA's with 2'-O-methyl modified nucleosides showed an increased duration of activity relative to unmodified siRNA.

Another group of researchers compared asRNA and siRNA and found almost identical target position effects, appearance of mRNA cleavage fragments and tolerance for mutational and chemical backbone modifications (Holen et al., et al., *Nucleic Acids Research*, 2003, 31(9), 2401-2407). They found that small numbers of 2'-O-methyl modified nucleosides gave good activity compared to wild type but that the activity lessened as the numbers of 2'-O-methyl modified nucleosides was increased.

In another recent report researchers looked at the effects of a variety of chemical modifications, including 2'-O-methyl, had on the activity and biological properties of siRNA (Ya-Lin Chiu and Tariq M. Rana, *RNA*, 2003, (9), 1034-1048). They showed that incorporation of 2'-O-methyl in the sense or antisense strand (fully modified strands) severely reduced their activity in siRNA's relative to unmodified siRNA. Incorporation into both strands uniformly completely abolished activity.

One group of researchers looked at the effects of 2'-O-methyl groups and other chemically modified siRNA's in mammalian cells (Braasch et al., *Biochemistry*, 2003, (42), 7967-7975). They showed that fully modified 2'-O—$CH_3$ siRNA did not inhibit gene expression in one or both strands.

In another study the placement of a 2'-O-methyl group at the 5'-terminus on the antisense strand was reported to severely limit activity whereas the 3'-terminus of the antisense and the 3' and 5'-termini of the sense strand were tolerated (Czauderna et al., *Nucleic Acids Research*, 2003, 31(11), 2705-2716). They also reported that internal 2'-O-methyls provide nuclease stability and when placed at particular positions internally they show good activity but less than unmodified siRNA. They also disclose siRNA constructs having alternating 2'-O-methyl nucleosides in both strands.

More recently 2'-OCH$_3$ modified nucleosides in alternating motifs with unmodified nucleosides have been reported (see Published U.S. Application Pub. No.: US 2004/0180351). Also, 2'-OCH$_3$ modified nucleosides have been used in combination with 2'-F as well as 2'-deoxy nucleosides to fully modify each strand of a duplex. The resulting siRNA duplexes are fully modified with the pyrimidines and purines of each strand uniformly modified with groups such as 2'-F, 2'-H or 2'-OCH$_3$ (see Published U.S. Applications Pub. Nos.: US 2003/0206887 and US2003/0143732).

Like the RNAse H pathway, the RNA interference pathway of antisense modulation of gene expression is an effective means for modulating the levels of specific gene products and may therefore prove to be uniquely useful in a number of therapeutic, diagnostic, and research applications involving gene silencing. The present invention therefore further provides compositions useful for modulating gene expression pathways, including those relying on an antisense mechanism of action such as RNA interference and dsRNA enzymes as well as non-antisense mechanisms. One having skill in the art, once armed with this disclosure will be able, without undue experimentation, to identify preferred compositions for these uses.

SUMMARY OF THE INVENTION

In one embodiment the present invention provides compositions comprising a first oligomeric compound and a second oligomeric compound wherein at least a portion of the first oligomeric compound is capable of hybridizing with at least a portion of the second oligomeric compound and at least a portion of the first oligomeric compound is complementary to and capable of hybridizing to a selected nucleic acid target. Both the first and second oligomeric compounds comprise alternating 2'-OCH$_3$ and 2'-F modified nucleosides linked by internucleoside linking groups.

In another embodiment of the present invention compositions are provided comprising a first oligomeric compound and a second oligomeric compound wherein at least a portion of the first oligomeric compound is capable of hybridizing with at least a portion of the second oligomeric compound and at least a portion of the first oligomeric compound is complementary to and capable of hybridizing to a selected nucleic acid target and the first oligomeric compound has the formula:

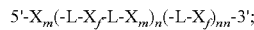

and the second oligomeric compound has the formula:

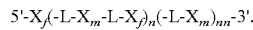

wherein
each L is, independently, an internucleoside linking group;
each X$_m$ is a 2'-OCH$_3$ modified nucleoside;
each X$_f$ is a 2'-F modified nucleoside;
n is 9 or 10;
nn is 0 or 1; and wherein the composition optionally further comprises one or more terminal phosphate moieties, terminal cap moieties or conjugate groups.

In a preferred embodiment the composition comprises two strands that align such that the 2'-OCH$_3$ modified nucleosides of the first oligomeric compound are complementary with and align with the 2'-F modified nucleosides of the second oligomeric compound in at least part of the hybridized portion of the composition.

In another preferred embodiment the 5'-terminal hybridizing nucleoside of the first oligomeric compound is a 2'-OCH$_3$ modified nucleoside and the 3'-terminal hybridizing nucleoside of the second oligomeric compound is a 2'-F modified nucleoside.

In another embodiment one or both of the first and second oligomeric compounds further comprises a 5'-terminal phosphate moiety wherein the phosphate moiety has the formula:

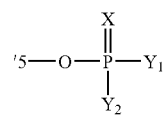

wherein
X is O or S;
Y$_1$ is OH or C$_1$-C$_4$ alkyl; and
Y$_2$ is H, OH or C$_1$-C$_4$ alkyl.

In another embodiment each of the internucleoside linking groups is, independently, a phosphodiester or a phosphorothioate internucleoside linking group.

In another embodiment the composition comprises at least one conjugate group.

In another embodiment at least one of the first and the second oligomeric compounds further comprises at least one terminal cap moiety attached at the 3'-end, the 5'-end or both the 3'-end and the 5'-end. In a preferred embodiment the terminal cap moiety is an inverted deoxy a basic moiety.

In one embodiment each of the first and second oligomeric compounds independently has from about 12 to about 24 nucleobases. In a more preferred embodiment each of the first and second oligomeric compounds independently has from about 19 to about 23 nucleobases. In another embodiment the first and the second oligomeric compounds form a complementary antisense/sense siRNA duplex.

In one embodiment a method of inhibiting protein levels in a tumor in an animal is provided comprising contacting the animal with a composition of the invention. In a preferred embodiment the method of contacting is via intravenous administration. In another embodiment the tumor is a glioblastoma. In a further embodiment the protein is encoded by the surviving gene.

In one embodiment each of the 2'-OCH$_3$ modified nucleosides of the first oligomeric compound align with a 2'-F modified nucleoside of the second oligomeric compound. In a preferred embodiment the compositions comprise a 2'-OCH$_3$ modified nucleoside at the 5'-terminus of the first oligomeric compound and a 2'-F modified nucleoside at the 3'-terminus of the second oligomeric compound. In another preferred the last hybridized nucleoside at the 5'-terminus of the first oligomeric compound is a 2'-OCH$_3$ modified nucleoside and the last hybridized nucleoside at 3'-terminus of the second oligomeric compound is a 2'-F modified nucleoside.

In one embodiment the first oligomeric compound further comprises a 5'-phosphate group. In another embodiment the second oligomeric compound further comprises a 5'-phosphate group. In a further embodiment the first and the second oligomeric compounds independently, comprise a 5'-phosphate group.

In one embodiment the first oligomeric compound comprises a 3'-terminal OH group.

In one embodiment the nucleosides of each of the first and the second oligomeric compounds are linked by phosphodiester internucleoside linking groups. In another embodiment the nucleosides of each of the first and the second oligomeric compounds are linked by phosphorothioate internucleoside linking groups. In a further embodiment the nucleosides of one of the first and the second oligomeric compound are linked by phosphorothioate internucleoside linking groups and the nucleosides of the other of the first and the second oligomeric compound are linked by phosphodiester internucleoside linking groups. In another embodiment the nucleosides of the first oligomeric compound are linked by phosphorothioate internucleoside linking groups and the nucleosides of the second oligomeric compound are linked by phosphodiester internucleoside linking groups.

In one embodiment each of the nucleosides of the first and the second oligomeric compound are independently linked by an internucleoside linking group selected from the group consisting of phosphodiester, phosphorothioate, chiral phosphorothioate, phosphorodithioate, phosphotriester, aminoalkylphosphotriester, methyl phosphonate, alkyl phosphonate, 5'-alkylene phosphonate, chiral phosphonate, phosphinate, phosphoramidate, 3'-amino phosphoramidate, aminoalkylphosphoramidate, thionophosphoramidate, thionoalkylphosphonate, thionoalkylphosphotriester, selenophosphate and boranophosphate.

In one embodiment at least one of the first and the second oligomeric compounds further comprises at least one conjugate group attached at the 3'-end, the 5'-end or both the 3'-end and the 5'-end.

In one embodiment at least one of the first and the second oligomeric compounds further comprises at least one terminal cap moiety attached at the 3'-end, the 5'-end or both the 3'-end and the 5'-end. In a preferred embodiment the terminal cap moiety is an inverted deoxy a basic moiety. In another embodiment one of the first and second oligomeric compounds is a sense strand and wherein the sense strand comprises a terminal cap moiety at one or both of the 3'-terminal and the 5'-terminal ends. In a preferred embodiment the terminal cap moiety is an inverted deoxy a basic moiety.

In one embodiment each of the first and second oligomeric compounds independently has from about 8 to about 80 nucleobases. In another embodiment each of the first and second oligomeric compounds independently has from about 10 to about 50 nucleobases. In a further embodiment each of the first and second oligomeric compounds independently has from about 12 to about 30 nucleobases.

In one embodiment the first and the second oligomeric compounds are a complementary pair of siRNA oligomeric compounds. In another embodiment the first and the second oligomeric compounds are an antisense/sense pair of oligomeric compounds. In a further embodiment the first oligomeric compound is an antisense oligomeric compound. In another embodiment the second oligomeric compound is a sense oligomeric compound.

DETAILED DESCRIPTION OF THE INVENTION

The present invention provides double stranded compositions wherein each strand comprises an alternating motif. The alternating motif of the present invention comprises 2'-OCH₃ modified nucleosides that alternate with 2'-F modified nucleosides. In a preferred aspect of the present invention the two strands hybridize such that the alternating 2'-OCH₃ modified nucleosides from one strand align with the 2'-F modified nucleosides of the other strand to give an alternating motif having an offset register. A preferred composition comprises an siRNA duplex having an offset register with the alignment such that the 5'-end of the antisense strand has a 5'-OCH₃ modified nucleoside as the terminal hybridizing nucleoside.

In one aspect the compositions comprising alternating motifs of the present invention mimic RNA by having all of the nucleosides modified with either 2'-OCH₃ or 2'-F which gives 3'-endo conformational geometry and enhances desired properties such as but not limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage.

In one aspect of the present invention compositions are provided comprising a first and a second oligomeric compound that are at least partially hybridized to form a duplex region and further comprising a region that is complementary to and hybridizes to a nucleic acid target. In one aspect the compositions include a first oligomeric compound that is an antisense strand having a complementary region to a nucleic acid target and a second oligomeric compound that is a sense strand having one or more regions of complementarity to and forming at least one duplex region with the first oligomeric compound.

Compositions of the present invention are useful for the modulation of gene expression. In one aspect of the present invention a targeted cell, group of cells, a tissue or an animal is contacted with a composition of the invention to effect reduction of mRNA that can directly inhibit gene expression. In another embodiment the reduction of mRNA indirectly upregulates a non-targeted gene through a pathway that relates the targeted gene to a non-targeted gene. Numerous methods and models for the regulation of genes using compositions of the invention are illustrated in the art and some are illustrated in the examples.

In one aspect the compositions of the invention modulate gene expression by hybridizing to a nucleic acid target resulting in loss of its normal function. As used herein, the term "target nucleic acid" or "nucleic acid target" is used for convenience to encompass any nucleic acid capable of being targeted including without limitation DNA, RNA (including pre-mRNA and mRNA or portions thereof) transcribed from such DNA, and also cDNA derived from such RNA. In a preferred embodiment of the invention the target nucleic acid is a messenger RNA. In a further preferred embodiment the degradation of the targeted messenger RNA is facilitated by an activated RISC complex that is formed with compositions of the invention. In another embodiment the degradation of the targeted messenger RNA is facilitated by a nuclease such as RNaseH.

The hybridization of a composition of the invention with its target nucleic acid is generally referred to as "antisense". Consequently, the preferred mechanism in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

The compositions and methods of the present invention are also useful in the study, characterization, validation and modulation of small non-coding RNAs. These include, but are not limited to, microRNAs (miRNA), small nuclear RNAs (snRNA), small nucleolar RNAs (snoRNA), small temporal RNAs (stRNA) and tiny non-coding RNAs (tncRNA) or their precursors or processed transcripts or their association with other cellular components.

Small non-coding RNAs have been shown to function in various developmental and regulatory pathways in a wide range of organisms, including plants, nematodes and mammals. MicroRNAs are small non-coding RNAs that are processed from larger precursors by enzymatic cleavage and inhibit translation of mRNAs. stRNAs, while processed from precursors much like miRNAs, have been shown to be involved in developmental timing regulation. Other non-coding small RNAs are involved in events as diverse as cellular splicing of transcripts, translation, transport, and chromosome organization.

As modulators of small non-coding RNA function, the compositions of the present invention find utility in the control and manipulation of cellular functions or processes such as regulation of splicing, chromosome packaging or methylation, control of developmental timing events, increase or decrease of target RNA expression levels depending on the timing of delivery into the specific biological pathway and translational or transcriptional control. In addition, the compositions of the present invention can be modified in order to optimize their effects in certain cellular compartments, such as the cytoplasm, nucleus, nucleolus or mitochondria.

The compositions of the present invention can further be used to identify components of regulatory pathways of RNA processing or metabolism as well as in screening assays or devices.

General Chemistry

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms with from 1 to about 6 carbon atoms being more preferred. Alkyl groups as used herein may optionally include one or more further substituent groups.

The term "alkenyl," as used herein, refers to a straight or branched hydrocarbon chain radical containing up to twenty four carbon atoms having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines, for example. Aliphatic groups as used herein may optionally include further substituent groups.

The term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

The terms "halo" and "halogen," as used herein, refer to an atom selected from fluorine, chlorine, bromine and iodine.

The terms "aryl" and "aromatic," as used herein, refer to a mono- or polycyclic carbocyclic ring system radical having one or more aromatic rings. Examples of aryl groups include, but not limited to, phenyl, naphthyl, tetrahydronaphthyl, indanyl, idenyl and the like. Aryl groups as used herein may optionally include further substituent groups.

The term "heterocyclic," as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain no heteroatoms. A heterocyclic group typically includes at least one atom selected from sulfur, nitrogen or oxygen. Examples of heterocyclic groups include, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

The terms "substituent and substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to the parent compound. Such groups include without limitation, halogen, hydroxyl, alkyl, alkenyl, alkynyl, acyl (—C(O)$R_a$), carboxyl (—C(O)O—$R_a$), aliphatic, alicyclic, alkoxy, substituted oxo (—O—$R_a$), aryl, aralkyl, heterocyclic, heteroaryl, heteroarylalkyl, amino (—$NR_bR_c$), imino(=$NR_b$), amido (—C(O)$NR_bR_c$ or —N($R_b$)C(O)$R_a$), azido (—$N_3$), nitro (—$NO_2$), cyano (—CN), carbamido (—OC(O)$NR_bR_c$ or —N($R_b$)C(O)O$R_a$), ureido (—N($R_b$)C(O)$NR_bR_c$), thioureido (—N($R_b$)C(S)$NR_bR_c$), guanidinyl (—N($R_b$)C(=$NR_b$)$NR_bR_c$), amidinyl (—C(=$NR_b$)$NR_bR_c$ or —N($R_b$)C($NR_b$)$R_a$), thiol (—$SR_b$), sulfinyl (—S(O)$R_b$), sulfonyl (—S(O)$_2R_b$) and sulfonamidyl (—S(O)$_2NR_bR_c$ or —N($R_b$)S(O)$_2R_b$). Wherein each $R_a$, $R_b$ and $R_c$ is a further substituent group with a preferred list including without limitation alkyl, alkenyl, alkynyl, aliphatic, alkoxy, acyl, aryl, aralkyl, heteroaryl, alicyclic, heterocyclic and heteroarylalkyl.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999).

Examples of hydroxyl protecting groups include, but are not limited to, benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl (BOC), isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl (Alloc), acetyl (Ac), formyl, chloroacetyl, trifluoroacetyl, methoxyacetyl, phenoxyacetyl, benzoyl (Bz), methyl, t-butyl, 2,2,2-trichloroethyl, 2-trimethylsilyl ethyl, 1,1-dimethyl-2-propenyl, 3-methyl-3-butenyl, allyl, benzyl (Bn), para-methoxybenzyldiphenylmethyl, triphenylmethyl (trityl), 4,4'-dimethoxytriphenylmethyl (DMT), substituted or unsubstituted 9-(9-phenyl)xanthenyl (pixyl), tetrahydrofuryl, methoxymethyl, methylthiomethyl, benzyloxymethyl, 2,2,2-trichloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are DMT and substituted or unsubstituted pixyl.

Examples of amino protecting groups include, but are not limited to, t-butoxycarbonyl (BOC), 9-fluorenylmethoxycarbonyl (Fmoc), benzyloxycarbonyl, and the like.

Examples of thiol protecting groups include, but are not limited to, triphenylmethyl (Trt), benzyl (Bn), and the like.

The synthesized compounds can be separated from a reaction mixture and further purified by a method such as column chromatography, high pressure liquid chromatography, precipitation, or recrystallization. Further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Mechanisms of Gene Modulation

The terms "antisense" or "antisense inhibition" as used herein refer to the hybridization of an oligomeric compound or a portion thereof with a selected target nucleic acid. Multiple antisense mechanisms exist by which oligomeric compounds can be used to modulate gene expression in mammalian cells. Such antisense inhibition is typically based upon hydrogen bonding-based hybridization of complementary strands or segments such that at least one strand or segment is cleaved, degraded, or otherwise rendered inoperable. In this regard, it is presently suitable to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA.

A commonly exploited antisense mechanism is RNase H-dependent degradation of a targeted RNA. RNase H is a ubiquitously expressed endonuclease that recognizes antisense DNA-RNA heteroduplexes, hydrolyzing the RNA strand. A further antisense mechanism involves the utilization of enzymes that catalyze the cleavage of RNA-RNA duplexes. These reactions are catalyzed by a class of RNAse enzymes including but not limited to RNAse III and RNAse L. The antisense mechanism known as RNA interference (RNAi) is operative on RNA-RNA hybrids and the like. Both RNase H-based antisense (usually using single-stranded compounds) and RNA interference (usually using double-stranded compounds known as siRNAs) are antisense mechanisms, typically resulting in loss of target RNA function.

Optimized siRNA and RNase H-dependent oligomeric compounds behave similarly in terms of potency, maximal effects, specificity and duration of action, and efficiency. Moreover it has been shown that in general, activity of dsRNA constructs correlated with the activity of RNase H-dependent single-stranded antisense oligomeric compounds targeted to the same site. One major exception is that RNase H-dependent antisense oligomeric compounds were generally active against target sites in pre-mRNA whereas siRNAs were not.

These data suggest that, in general, sites on the target RNA that were not active with RNase H-dependent oligonucleotides were similarly not good sites for siRNA. Conversely, a significant degree of correlation between active RNase H oligomeric compounds and siRNA was found, suggesting that if a site is available for hybridization to an RNase H oligomeric compound, then it is also available for hybridization and cleavage by the siRNA complex. Consequently, once suitable target sites have been determined by either antisense approach, these sites can be used to design constructs that operate by the alternative antisense mechanism (Vickers et al., 2003, *J. Biol. Chem.* 278, 7108). Moreover, once a site has been demonstrated as active for either an RNAi or an RNAse H oligomeric compound, a single-stranded RNAi oligomeric compound (ssRNAi or asRNA) can be designed.

In some embodiments of the present invention, double-stranded antisense oligomeric compounds are suitable. These double-stranded antisense oligomeric compounds may be RNA or RNA-like, and may be modified or unmodified, in that modified oligomeric compounds retain the properties of forming an RNA:RNA hybrid and recruitment and (activation) of a dsRNase. In other embodiments, the single-stranded oligomeric compounds (ssRNAi or asRNA) may be RNA-like.

The oligomeric compounds and methods of the present invention are also useful in the study, characterization, validation and modulation of small non-coding RNAs. These include, but are not limited to, microRNAs (miRNA), small nuclear RNAs (snRNA), small nucleolar RNAs (snoRNA), small temporal RNAs (stRNA) and tiny non-coding RNAs (tncRNA) or their precursors or processed transcripts or their association with other cellular components.

Small non-coding RNAs have been shown to function in various developmental and regulatory pathways in a wide range of organisms, including plants, nematodes and mammals. MicroRNAs are small non-coding RNAs that are processed from larger precursors by enzymatic cleavage and inhibit translation of mRNAs. stRNAs, while processed from precursors much like miRNAs, have been shown to be involved in developmental timing regulation. Other non-coding small RNAs are involved in events as diverse as cellular splicing of transcripts, translation, transport, and chromosome organization.

As modulators of small non-coding RNA function, the oligomeric compounds of the present invention find utility in the control and manipulation of cellular functions or processes such as regulation of splicing, chromosome packaging or methylation, control of developmental timing events, increase or decrease of target RNA expression levels depending on the timing of delivery into the specific biological pathway and translational or transcriptional control. In addition, the oligomeric compounds of the present invention can be modified in order to optimize their effects in certain cellular compartments, such as the cytoplasm, nucleus, nucleolus or mitochondria.

The compounds of the present invention can further be used to identify components of regulatory pathways of RNA processing or metabolism as well as in screening assays or devices.

Oligomeric Compounds

The term "nucleoside," as used herein, refers to a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. Within the oligonucleotide structure, the phosphate groups are commonly referred to as forming the internucleoside linkages of the oligonucleotide, or in conjunction with the sugar ring, the backbone of the oligonucleotide. In forming oligonucleotides, the phosphate groups covalently link adjacent nucleosides to one another to form a linear polymeric compound. The normal internucleoside linkage of RNA and DNA is a 3' to 5' phosphodiester linkage.

In the context of this invention, the term "oligonucleoside" refers to a sequence of nucleosides that are joined by internucleoside linkages that do not have phosphorus atoms. Internucleoside linkages of this type are further described in the "modified internucleoside linkage" section below.

The term "oligonucleotide," as used herein, refers to an oligomer or polymer of ribonucleic acid (RNA) or deoxyribonucleic acid (DNA) composed of naturally occurring nucleobases, sugars and phosphodiester internucleoside linkages.

The terms "oligomer" and "oligomeric compound," as used herein, refer to a plurality of naturally occurring and/or non-naturally occurring nucleosides, joined together in a specific sequence, to form a polymeric structure. It is preferable that oligomeric compounds be capable of hybridizing a region of a target nucleic acid. Included in the terms "oligomer" and "oligomeric compound" are oligonucleotides, oligonucleotide analogs, oligonucleotide mimetics, oligonucleosides and chimeric combinations of these, and are thus intended to be broader than the term "oligonucleotide," including all oligomers having all manner of modifications including but not limited to those known in the art. Oligomeric compounds are typically structurally distinguishable from, yet functionally interchangeable with, naturally-occurring or synthetic wild-type oligonucleotides. Thus, oligomeric compounds include all such structures that function effectively to mimic the structure and/or function of a desired RNA or DNA strand, for example, by hybridizing to a target. Such non-naturally occurring oligonucleotides are often desired over the naturally occurring forms because they often have enhanced properties, such as for example, enhanced cellular uptake, enhanced affinity for nucleic acid target and increased stability in the presence of nucleases.

Oligomeric compounds can include double-stranded constructs such as, for example, two oligomeric compounds forming a double stranded hybridized construct or a single strand with sufficient self complementarity to allow for hybridization and formation of a fully or partially double-stranded compound. In one embodiment of the invention, double-stranded oligomeric compounds encompass short interfering RNAs (siRNAs). As used herein, the term "siRNA" is defined as a double-stranded construct comprising a first and second strand and having a central complementary portion between the first and second strands and terminal portions that are optionally complementary between the first and second strands or with a target nucleic acid. Each strand in the complex may have a length as defined above and may further comprise a central complementary portion having one of these defined lengths. Each strand may further comprise a terminal unhybridized portion having from 1 to about 6 nucleobases in length. The siRNAs may also have no terminal portions (overhangs). The two strands of an siRNA can be linked internally leaving free 3' or 5' termini or can be linked to form a continuous hairpin structure or loop. The hairpin structure may contain an overhang on either the 5' or 3' terminus producing an extension of single-stranded character.

In one embodiment of the invention, double-stranded constructs are canonical siRNAs. As used herein, the term "canonical siRNA" is defined as a double-stranded oligomeric compound having a first strand and a second strand each strand being 21 nucleobases in length with the strands being complementary over 19 nucleobases and having on each 3' termini of each strand a deoxy thymidine dimer (dTdT) which in the double-stranded compound acts as a 3' overhang.

In another embodiment, the double-stranded constructs are blunt-ended siRNAs. As used herein the term "blunt-ended siRNA" is defined as an siRNA having no terminal overhangs. That is, at least one end of the double-stranded constructs is blunt. siRNAs whether canonical or blunt act to elicit dsRNAse enzymes and trigger the recruitment or activation of the RNAi antisense mechanism. In a further embodiment, single-stranded RNAi (ssRNAi) compounds that act via the RNAi antisense mechanism are contemplated.

Further modifications can be made to the double-stranded compounds and may include conjugate groups attached to one of the termini, selected nucleobase positions, sugar positions or to one of the internucleoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double-stranded. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

The oligomeric compounds in accordance with this invention preferably comprise from about 8 to about 80 nucleobases (i.e. from about 8 to about 80 linked nucleosides/monomeric subunits). One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the oligomeric compounds of the invention are 10 to 50 nucleobases in length. One having ordinary skill in the art will appreciate that this embodies oligomeric compounds of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the oligomeric compounds of the invention are 12 to 30 nucleobases in length. One having ordinary skill in the art will appreciate that this embodies oligomeric compounds of 12, 13, 14, 15, 16, 17, 18, 19, 20, 21, 22, 23, 24, 25, 26, 27, 28, 29, or 30 nucleobases in length.

In a further preferred embodiment, the oligomeric compounds of the invention are 12 to 24 nucleobases in length. One having ordinary skill in the art will appreciate that this embodies oligomeric compounds of 12, 13, 14, 15, 16, 17, 18, 19, 20, 21, 22, 23 or 24 nucleobases in length.

In a further preferred embodiment, the oligomeric compounds of the invention are 19 to 23 nucleobases in length. One having ordinary skill in the art will appreciate that this embodies oligomeric compounds of 19, 20, 21, 22 or 23 nucleobases in length.

One particularly preferred length for oligomeric compounds is from about 12 to about 30 nucleobases. Another particularly preferred length is from about 12 to about 24 nucleobases. A further particularly preferred length is from about 19 to about 23 nucleobases.

Modified Sugars

The term "modified sugar," as used herein, refers to modifications of native ribofuranose and deoxyribofuranose sugars used in the nucleosides and oligomeric compounds of the invention. Modified sugars comprise nucleosides where the heterocyclic base moiety or modified heterocyclic base moiety is typically maintained for hybridization with an appropriate target nucleic acid. Such "modified sugars" are often desired over the naturally occurring forms because of advantageous properties they can impart to an oligomeric compound such as, for example, enhanced cellular uptake, enhanced affinity for nucleic acid target and increased stability to nuclease degradation. The term "modified sugar" is intended to include all manner of modifications known in the art including without limitation modifications to ring atoms and/or addition of substituent groups.

The terms used to describe the conformational geometry of homoduplex nucleic acids are "A Form" for RNA and "B Form" for DNA, (determined from X-ray diffraction analysis of nucleic acid fibers, (see Arnott et al., *Biochem. Biophys. Res. Comm.,* 1970, 47, 1504). In general, RNA:RNA duplexes are more stable and have higher melting temperatures (Tm's) than DNA:DNA duplexes (Sanger, Principles of Nucleic Acid Structure, 1984, Springer-Verlag; New York, N.Y.; Lesnik et al., *Biochemistry,* 1995, 34, 10807-10815; Conte et al., *Nucleic Acids Res.,* 1997, 25, 2627-2634). The increased stability of RNA has been attributed to several structural features, most notably the improved base stacking interactions that result from an A-form geometry (Searle et al., *Nucleic Acids Res.,* 1993, 21, 2051-2056). The presence of the 2 hydroxyl in RNA biases the sugar toward a C3' endo pucker (also designated a Northern pucker), which causes the duplex to favor the A-form geometry. The 2' hydroxyl groups of RNA also form a network of water mediated hydrogen bonds that help stabilize the RNA duplex (Egli et al., *Biochemistry,* 1996, 35, 8489-8494). Deoxy nucleic acids prefer a C2' endo sugar pucker, (Southern pucker) imparting a less stable B-form geometry (Sanger, Principles of Nucleic Acid Structure, 1984, Springer-Verlag; New York).

DNA:RNA hybrid duplexes are usually less stable than RNA:RNA duplexes, and depending on their sequence, may be either more or less stable than DNA:DNA duplexes (Searle et al., *Nucleic Acids Res.,* 1993, 21, 2051-2056). The structure of a hybrid duplex is intermediate between A- and B-form geometries, which may result in poor stacking interactions (Lane et al., *Eur. J. Biochem.,* 1993, 215, 297-306; Fedoroff et al., *J. Mol. Biol.,* 1993, 233, 509-523; Gonzalez et al., *Biochemistry,* 1995, 34, 4969-4982; Horton et al., *J. Mol. Biol.,* 1996, 264, 521-533).

The stability of the duplex formed between a target RNA strand and a synthetic oligomeric strand is central to antisense therapies mediated by mechanisms such as, but not limited to, RNase H and RNA interference. Oligomeric compounds are also useful in antisense therapies by blocking transcription, blocking translation and in modulating splicing events. In the case of RNase H mediated gene modulation, effective mRNA inhibition requires a very high binding affinity between the RNA target and the oligomeric compound and also requires an RNA/DNA region where the enzyme effects degradation of the RNA strand. The triggering of RNA interference requires A form duplex geometry (i.e. predominantly 3'-endo) between the RNA target and the oligomeric compound. Substitution of modified nucleosides having 3'-endo conformational geometry in place of native RNA nucleosides can enhance the overall properties and activity of oligomeric compounds. Such enhanced properties include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage.

The relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent.

In one aspect modified sugars include sugars comprising a substituent group. Such sugars can be referred to as a "substituted sugar" or "substituted sugar moiety. The substituent group can replace a hydrogen or other group thereby being an added substituent or a substituent that replaces a group such as the 2'-hydroxyl group of native RNA. Oligomeric compounds of the invention may contain one or more substituted sugar moieties and the substituent groups may vary from one nucleoside to another or may form regions or alternating motifs. These substituted sugar moieties may contain one, two, three, four or five substituents, at any position(s) on the sugar ring (namely 1', 2', 3', 4', or 5'). Oligomeric compounds are preferably modified at one or more positions including the 5'-position of the 5'-terminus, the 3'-position of the 3'-terminus, at any 2'-position of any nucleoside for 3'-5'-linked regions or at any 3'-position of any nucleoside for a 2'-5'-linked region. A more preferred substitution it the 2'-position of a 3'-5'-linked region.

The basic furanose ring system can be chemically manipulated in a number of different ways. The configuration of attachment of the heterocyclic base to the 1'-position can result in the α-anomer (down) or the β-anomer (up). The β-anomer is the anomer found in native DNA and RNA but both forms can be used to prepare oligomeric compounds. A further manipulation can be achieved through the substitution the native form of the furanose with the enantiomeric form e.g. replacement of a native D-furanose with its mirror image enantiomer, the L-furanose. Another way to manipulate the furanose ring system is to prepare stereoisomers such as for example substitution at the 2'-position to give either the ribofuranose (down) or the arabinofuranose (up) or substitution at the 3'-position to give the xylofuranose or by altering the 2', and the 3'-position simultaneously to give a lyxofuranose. The use of stereoisomers of the same substituent can give rise to completely different conformational geometry such as for example 2'-F which is 3'-endo in the ribo configuration and 2'-endo in the arabino configuration.

Suitable sugar substituent groups include, but are not limited to: hydroxyl, F, Cl, Br, SH, CN, OCN, $CF_3$, $OCF_3$, $SOCH_3$, $SO_2CH_3$, nitrate ester ($ONO_2$), $NO_2$, $N_3$, $NH_2$, O—, S—, or $N(R_k)$-alkly; O—, S—, or $N(R_k)$-alkenyl; O—, S— or $N(R_k)$-alkynyl; O-alkylenyl-O-alkyl, alkynyl, alkaryl, aralkyl, O-alkaryl, O-aralkyl, a heterocyclic group linked to the sugar through an alkylenyl group, an aryl group further substituted with a heterocyclic group linked to the aryl group through an alkylenyl group, an amino group further substituted with an aminoalkylenyl group, polyalkylenylamino, substituted silyl, an RNA cleaving group, a reporter group, an intercalator, a group for improving the pharmacokinetic properties of an oligonucleotide, and a group for improving the pharmacodynamic properties of an oligonucleotide, wherein the substituent groups are optionally substituted with further substituent groups as previously defined.

Preferred sugar substituent groups are selected from: hydroxyl, F, O—, S—, or $N(R_k)$-alkyl; O—, S—, or $N(R_k)$-alkenyl; O—, S— or $N(R_k)$-alkynyl; or O-alkylene-O-alkyl, including $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nH]_2$, where n and m are from 1 to about 10 and wherein the substituent groups are optionally substituted with further substituent groups as previously defined.

Preferred 2'-sugar substituent groups include F, methoxy (—O—$CH_3$), aminopropoxy (—O($CH_2$)$_3NH_2$), allyl (—$CH_2$—CH=$CH_2$), allyloxy (—O—$CH_2$—CH=$CH_2$), methoxyethoxy (—$OCH_2CH_2OCH_3$, also known as 2'-MOE) (Martin et al., *Helv. Chim. Acta*, 1995, 78, 486-504), dimethylaminooxyethoxy (—O($CH_2$)$_2$ON($CH_3$)$_2$ or DMAOE), and dimethylaminoethoxyethoxy (—O($CH_2$)$_2$O($CH_2$)$_2$N($CH_3$)$_2$, also known as —O-dimethylaminoethoxyethyl or DMAEOE).

Nucleobases and Modified Nucleobases

As used herein the term "heterocyclic base moiety" refers to nucleobases and modified or substitute nucleobases used to form nucleosides of the invention. The term "heterocyclic base moiety" includes unmodified nucleobases such as the native purine bases adenine (A) and guanine (G), and the pyrimidine bases thymine (T), cytosine (C) and uracil (U). The term is also intended to include all manner of modified or substitute nucleobases including but not limited to synthetic and natural nucleobases such as xanthine, hypoxanthine, 2-aminopyridine and 2-pyridone, 5-methylcytosine (5-me-C), 5-hydroxymethylenyl cytosine, 2-amino and 2-fluoroadenine, 2-propyl and other alkyl derivatives of adenine and guanine, 2-thio cytosine, uracil, thymine, 3-deaza guanine and adenine, 4-thiouracil, 5-uracil (pseudouracil), 5-propynyl (—C≡C—$CH_3$) uracil and cytosine and other alkynyl derivatives of pyrimidine bases, 5-halo particularly 5-bromo, 5-trifluoromethyl and other 5-substituted uracils and cytosines, 6-methyl and other alkyl derivatives of adenine and guanine, 6-azo uracil, cytosine and thymine, 7-methyl adenine and guanine, 7-deaza adenine and guanine, 8-halo, 8-amino, 8-aza, 8-thio, 8-thioalkyl, 8-hydroxyl and other 8-substituted adenines and guanines, universal bases, hydrophobic bases, promiscuous bases, size-expanded bases, and fluorinated bases as defined herein. Further modified nucleobases include tricyclic pyrimidines such as phenoxazine cytidine (1H-pyrimido[5,4-b][1,4]benzoxazin-2(3H)-one) and phenothiazine cytidine (1H-pyrimido[5,4-b][1,4]benzothiazin-2(3H)-one).

Further nucleobases (and nucleosides comprising the nucleobases) include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, those disclosed in Limbach et al., *Nucleic Acids Research*, 1994, 22(12), 2183-2196, and those disclosed by Sanghvi, Y. S., Chapter 15, *Antisense Research and Applications*, pages 289-302, Crooke, S. T. and Lebleu, B., ed., CRC Press, 1993.

Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyl-adenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are especially useful when combined with 2'-O-methoxyethyl (2'-MOE) sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,681,941, and 5,750,692.

The term "universal base" as used herein, refers to a moiety that may be substituted for any base. The universal base need not contribute to hybridization, but should not significantly detract from hybridization and typically refers to a monomer in a first sequence that can pair with a naturally occuring base, i.e A, C, G, T or U at a corresponding position in a second sequence of a duplex in which one or more of the following is true: (1) there is essentially no pairing (hybridization) between the two; or (2) the pairing between them occurs non-discriminantly with the universal base hybridizing one or more of the the naturally occurring bases and without significant destabilization of the duplex. Exemplary universal bases include, without limitation, inosine, 5-nitroindole and 4-nitrobenzimidazole.

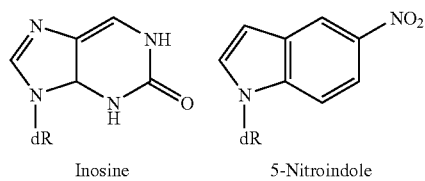

Inosine     5-Nitroindole

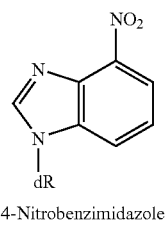

4-Nitrobenzimidazole

Additional examples of universal bases include, but are not limited to, those shown below. For further examples and descriptions of universal bases see Survey and summary: the applications of universal DNA base analogs. Loakes, D. *Nucleic Acids Research*, 2001, 29, 12, 2437-2447.

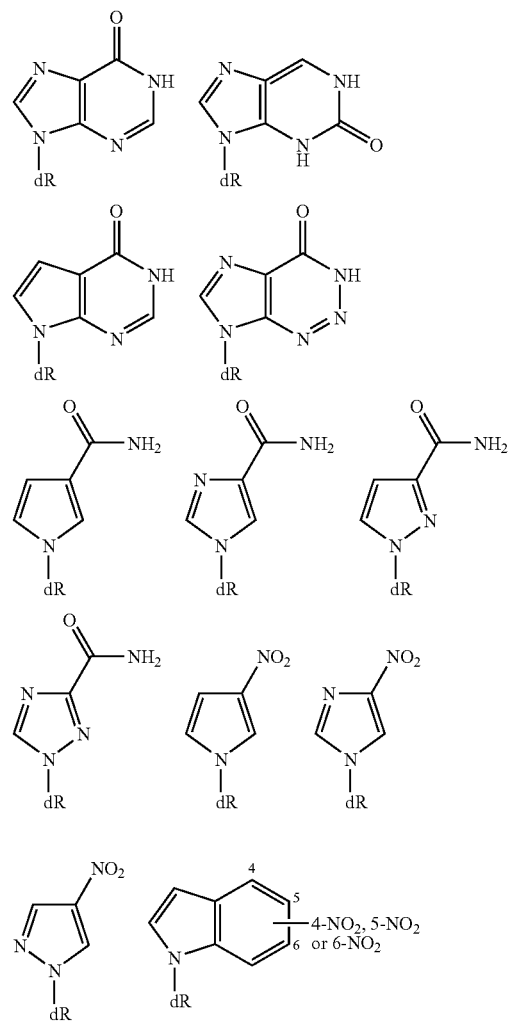

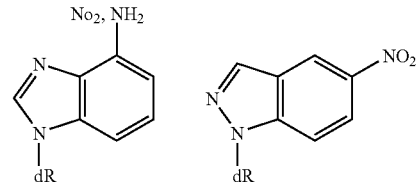

-continued

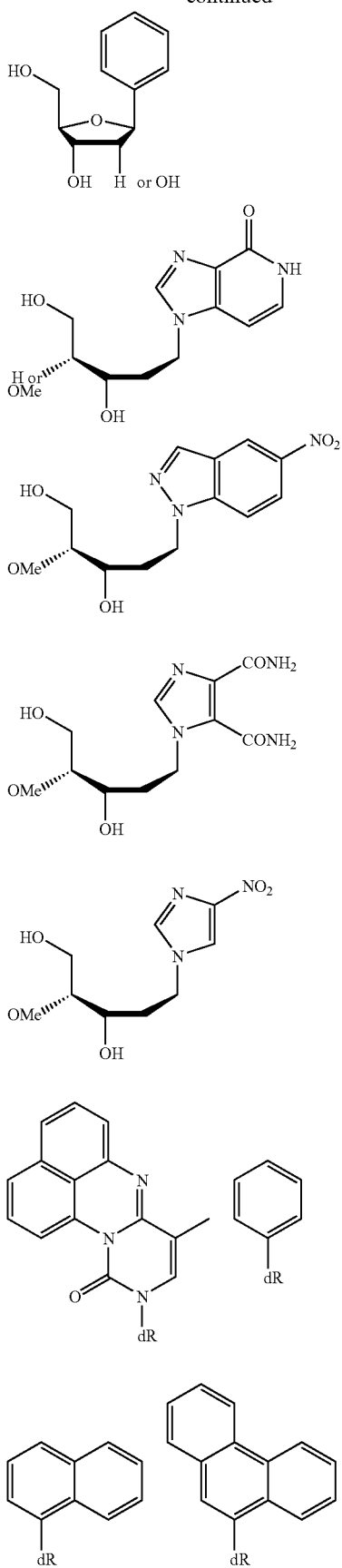

-continued

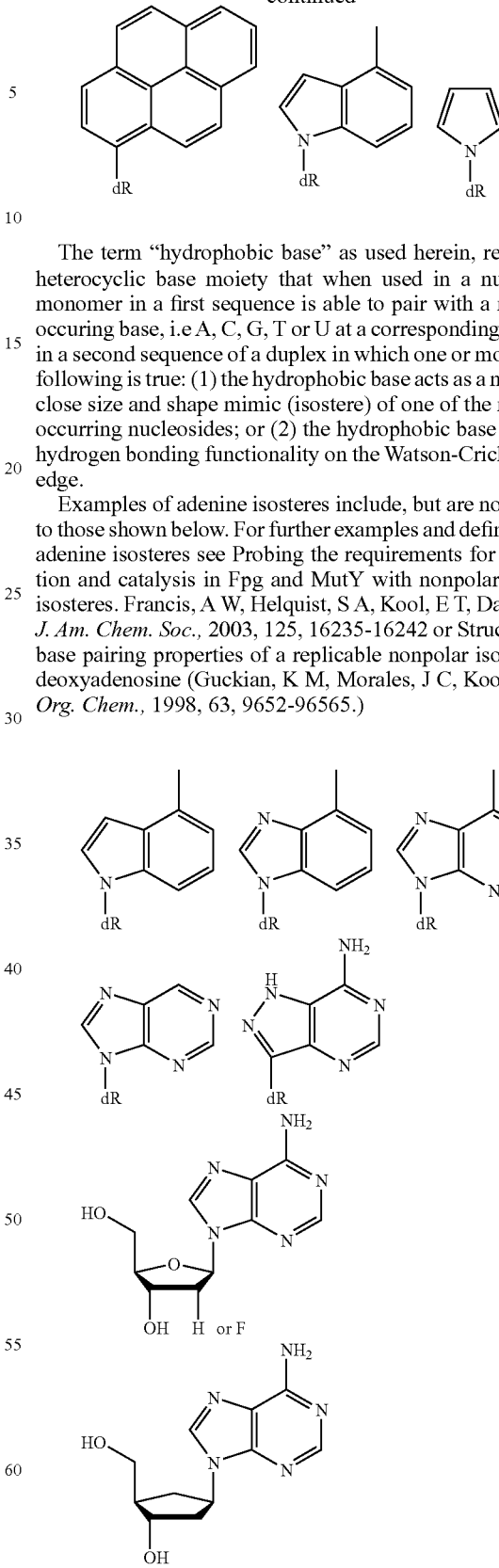

The term "hydrophobic base" as used herein, refers to a heterocyclic base moiety that when used in a nucleoside monomer in a first sequence is able to pair with a naturally occuring base, i.e A, C, G, T or U at a corresponding position in a second sequence of a duplex in which one or more of the following is true: (1) the hydrophobic base acts as a non-polar close size and shape mimic (isostere) of one of the naturally occurring nucleosides; or (2) the hydrophobic base lacks all hydrogen bonding functionality on the Watson-Crick pairing edge.

Examples of adenine isosteres include, but are not limited to those shown below. For further examples and definitions of adenine isosteres see Probing the requirements for recognition and catalysis in Fpg and MutY with nonpolar adenine isosteres. Francis, A W, Helquist, S A, Kool, E T, David, S S. *J. Am. Chem. Soc.*, 2003, 125, 16235-16242 or Structure and base pairing properties of a replicable nonpolar isostere for deoxyadenosine (Guckian, K M, Morales, J C, Kool, E T. *J. Org. Chem.*, 1998, 63, 9652-96565.)

A non-limiting example of a cytosine isostere is 2-fluoro4-methylbenzene deoxyribonucleoside, shown below. For additional information on cytosine isosteres see Hydrolysis of RNA/DNA hybrids containing nonpolar pyrimidine isosteres defines regions essential for HIV type polypurine tract selection. Rausch, J W, Qu, J, Yi-Brunozzi H Y, Kool, E T, LeGrice, S F J. *Proc. Natl. Acad. Sci.,* 2003, 100, 11279-11284.

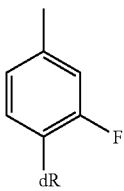

A non-limiting example of a guanosine isostere is 4-fluoro-6-methylbenzimidazole deoxyribonucleoside, shown below. For additional information on guanosine isosteres, see A highly effective nonpolar isostere of doeoxguanosine: synthesis, structure, stacking and base pairing (O'Neil, B M, Ratto, J E, Good, K L, Tahmassebi, D C, Helquist, S A, Morales, J C, Kool, E T. *J. Org. Chem.,* 2002, 67, 5869-5875.)

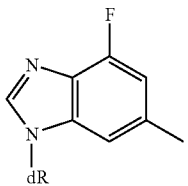

A non-limiting example of a thymidine isostere is 2,4-difluoro-5-toluene deoxyribonucleoside, shown below. For additional information on thymidine isosteres see: Moran, S, Ren, R X-F, Kool, E T. *Proc. Natl. Acad. Sci.,* 1997, 94, 10506-10511 or *J. Am. Chem. Soc.* 1997, 119, 2056-2057.

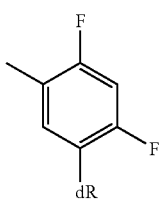

The term "promiscuous base" as used herein, refers to a monomer in a first sequence that can pair with a naturally occuring base, i.e A, C, G, T or U at a corresponding position in a second sequence of a duplex in which the promiscuous base can pair non-discriminantly with more than one of the naturally occurring bases, i.e. A, C, G, T, U. Non-limiting examples of promiscuous bases are 6H,8H-3,4-dihydropyrimido[4,5-c][1,2]oxazin-7-one and $N^6$-methoxy-2,6-diaminopurine, shown below. For further information, see Polymerase recognition of synthetic oligodeoxyribonucleotides incorporating degenerate pyrimidine and purine bases. Hill, F.; Loakes, D.; Brown, D. M. *Proc. Natl. Acad. Sci.,* 1998, 95, 4258-4263.

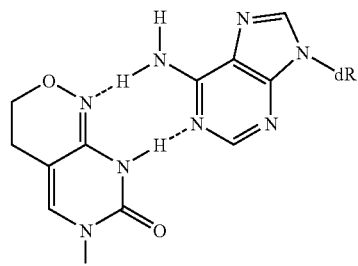

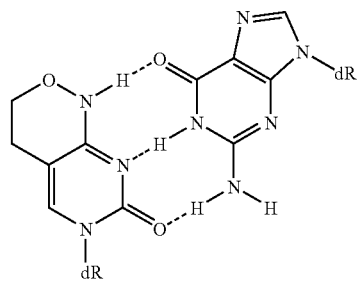

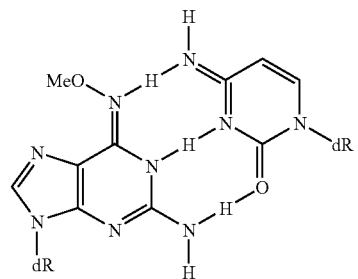

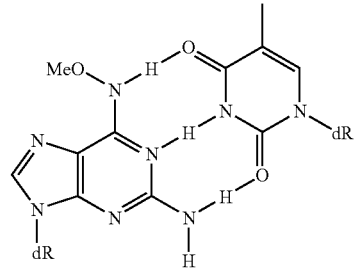

The term "size expanded base" as used herein, refers to analogs of naturally occurring nucleobases that are larger in size and retain their Watson-Crick pairing ability. Two non-limiting examples of size-expanded bases are shown below. For further discussions of size expanded bases see Liu et al., *Science,* 2003, 302, 868-871; Liu et al., *J. Am. Chem. Soc.* 2004, 126, 1102-1109; and Gao et al., *J. Am. Chem. Soc.* 2004, 126, 11826-11831.

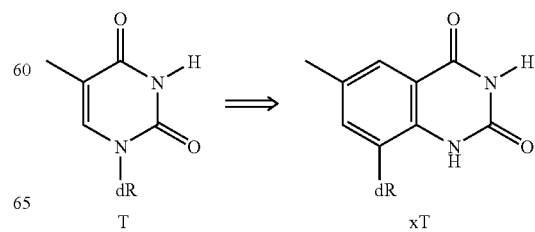

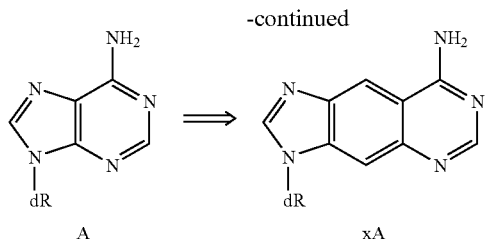

A → xA

The term "fluorinated nucleobase" as used herein, refers to a nucleobase or nucleobase analog, wherein one or more of the aromatic ring substituents is a fluorine atom. It may be possible that all of the ring substituents are fluorine atoms. Some non-limiting examples of fluorinated nucleobase are shown below. For further examples of fluorinated nucleobases see Lai et al., *Angew. Chem. Int. Ed.,* 2003, 42, 5973-5977; Lai et al., *J. Am. Chem. Soc.,* 2004, 126, 3040-3041; Kloppfer et al., *Nucleosides, Nucleotides & Nucleic Acids,* 2003, 22, 1347-1350; and Klopffer et al., *Chem Bio Chem.,* 2003, 5, 707-716.

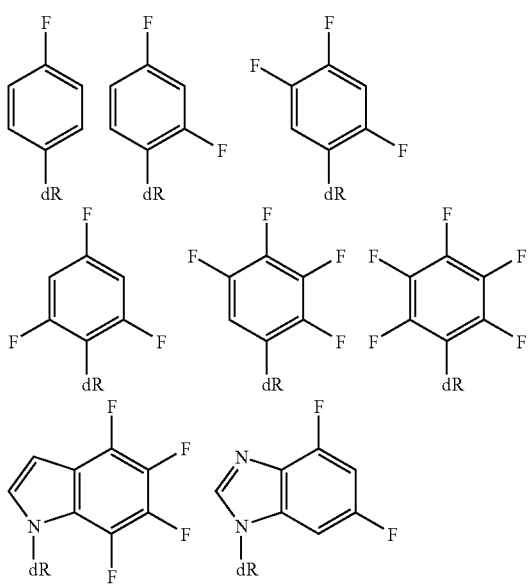

Other modified nucleobases include polycyclic heterocyclic moieties, which are routinely used in antisense applications to increase the binding properties of the modified strand to a target strand. The most studied modifications are targeted to guanosines hence they have been termed G-clamps or cytidine analogs.

Examples of G-clamps include substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one) and pyridoindole cytidine (H-pyrido[3',2':4,5]pyrrolo[2,3-d]pyrimidin-2-one).

Representative cytosine analogs that make 3 hydrogen bonds with a guanosine in a second oligonucleotide include 1,3-diazaphenoxazine-2-one (Kurchavov, et al., *Nucleosides and Nucleotides,* 1997, 16, 1837-1846), 1,3-diazaphenothiazine-2-one (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one (Wang, J.; Lin, K.-Y., Matteucci, M. Tetrahedron Lett. 1998, 39, 8385-8388). When incorporated into oligonucleotides these base modifications hybridized with complementary guanine (the latter also hybridized with adenine) and enhanced helical thermal stability by extended stacking interactions (see U.S. patent application Ser. No. 10/013,295).

Modified Internucleoside Linkages

The terms "modified internucleoside linkage" and "modified backbone," or simply "modified linkage" as used herein, refer to modifications or replacement of the naturally occurring phosphodiester internucleoside linkage connecting two adjacent nucleosides within an oligomeric compound. Such modified linkages include those that have a phosphorus atom and those that do not have a phosphorus atom.

Internucleoside linkages containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be a basic (the nucleobase is missing or has a hydroxyl group in place thereof). Various salts, mixed salts and free acid forms are also included. Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

In the *C. elegans* system, modification of the internucleotide linkage (phosphorothioate in place of phosphodiester) did not significantly interfere with RNAi activity, indicating that oligomeric compounds of the invention can have one or more modified internucleoside linkages, and retain activity. Indeed, such modified internucleoside linkages are often desired over the naturally occurring phosphodiester linkage because of advantageous properties they can impart such as, for example, enhanced cellular uptake, enhanced affinity for nucleic acid target and increased stability in the presence of nucleases.

Another phosphorus containing modified internucleoside linkage is the phosphonomonoester (see U.S. Pat. Nos. 5,874,553 and 6,127,346). Phosphonomonoester nucleic acids have useful physical, biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

As previously defined an oligonucleoside refers to a sequence of nucleosides that are joined by internucleoside linkages that do not have phosphorus atoms. Non-phosphorus containing internucleoside linkages include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts. Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Some additional examples of modified internucleoside linkages that do not contain a phosphorus atom therein include, —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester internucleotide linkage is represented as —O—P(=O)(OH)—O—$CH_2$—). The MMI type and amide internucleoside linkages are disclosed in the below referenced U.S. Pat. Nos. 5,489,677 and 5,602,240, respectively.

Conjugates

Another modification that can enhance the properties of an oligomeric compound or can be used to track the oligomeric compound or its metabolites is the attachment of one or more moieties or conjugates. Properties that are typically enhanced include without limitation activity, cellular distribution and cellular uptake. In one embodiment, such modified oligomeric compounds are prepared by covalently attaching conjugate groups to functional groups available on an oligomeric compound such as hydroxyl or amino functional groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve properties including but not limited to oligomer uptake, enhance oligomer resistance to degradation, and/or strengthen sequence-specific hybridization with RNA. Groups that enhance the pharmacokinetic properties, in the context of this invention, include groups that improve properties including but not limited to oligomer uptake, distribution, metabolism and excretion. Representative conjugate groups are disclosed in International Patent Application PCT/US92/09196.

Conjugate groups include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130.

Representative U.S. patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. The terms "cap structure" or "terminal cap moiety," as used herein, refer to chemical modifications, which can be attached to one or both of the termini of an oligomeric compound. These terminal modifications protect the oligomeric compounds having terminal nucleic acid moieties from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

Particularly preferred 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-di-amino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide;

phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925 and Published U.S. Patent Application Publication Number US 2005/0020525 published on Jan. 27, 2005).

Further 3' and 5'-stabilizing groups that can be used to cap one or both ends of an oligomeric compound to impart nuclease stability include those disclosed in WO 03/004602.

Oligomer Synthesis

Oligomerization of modified and unmodified nucleosides is performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA:Protein Interactions, Ed. Smith (1998), 1-36. Gallo et al., Tetrahedron (2001), 57, 5707-5713) synthesis as appropriate. In addition specific protocols for the synthesis of oligomeric compounds of the invention are illustrated in the examples below.

Oligonucleotides are generally prepared either in solution or on a support medium, e.g. a solid support medium. In general a first synthon (e.g. a monomer, such as a nucleoside) is first attached to a support medium, and the oligonucleotide is then synthesized by sequentially coupling monomers to the support-bound synthon. This iterative elongation eventually results in a final oligomeric compound or other polymer such as a polypeptide. Suitable support medium can be soluble or insoluble, or may possess variable solubility in different solvents to allow the growing support bound polymer to be either in or out of solution as desired. Traditional support medium such as solid support media are for the most part insoluble and are routinely placed in reaction vessels while reagents and solvents react with and/or wash the growing chain until the oligomer has reached the target length, after which it is cleaved from the support and, if necessary further worked up to produce the final polymeric compound. More recent approaches have introduced soluble supports including soluble polymer supports to allow precipitating and dissolving the iteratively synthesized product at desired points in the synthesis (Gravert et al., Chem. Rev., 1997, 97, 489-510).

The term support medium is intended to include all forms of support known to one of ordinary skill in the art for the synthesis of oligomeric compounds and related compounds such as peptides. Some representative support medium that are amenable to the methods of the present invention include but are not limited to the following: controlled pore glass (CPG); oxalyl-controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, Angew. Chem. Internal. Ed. 1972, 11, 314, sold under the trademark "PORASIL E" by Waters Associates, Framingham, Mass., USA); the mono ester of 1,4-dihydroxymethylenylbenzene and silica (see Bayer and Jung, Tetrahedron Lett., 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix or POROS, a copolymer of polystyrene/divinylbenzene (available from Perceptive Biosystems); soluble support medium, polyethylene glycol PEG's (see Bonora et al., Organic Process Research & Development, 2000, 4, 225-231).

Support bound oligonucleotide synthesis relies on sequential addition of nucleotides to one end of a growing chain. Typically, a first nucleoside (having protecting groups on any exocyclic amine functionalities present) is attached to an appropriate glass bead support and nucleotides bearing the appropriate activated phosphite moiety, i.e. an "activated phosphorous group" (typically nucleotide phosphoramidites, also bearing appropriate protecting groups) are added stepwise to elongate the growing oligonucleotide. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725, 677 and Re. 34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

The term "linking moiety," as used herein is generally a bi-functional group, covalently binds the ultimate 3'-nucleoside (and thus the nascent oligonucleotide) to the solid support medium during synthesis, but which is cleaved under conditions orthogonal to the conditions under which the 5'-protecting group, and if applicable any 2'-protecting group, are removed. Suitable linking moietys include, but are not limited to, a divalent group such as alkylene, cycloalkylene, arylene, heterocyclyl, heteroarylene, and the other variables are as described above. Exemplary alkylene linking moietys include, but are not limited to, $C_1$-$C_{12}$ alkylene (e.g. preferably methylene, ethylene (e.g. ethyl-1,2-ene), propylene (e.g. propyl-1,2-ene, propyl-1,3-ene), butylene, (e.g. butyl-1,4-ene, 2-methylpropyl-1,3-ene), pentylene, hexylene, heptylene, octylene, decylene, dodecylene), etc. Exemplary cycloalkylene groups include $C_3$-$C_{12}$ cycloalkylene groups, such as cyclopropylene, cyclobutylene, cyclopentanyl-1,3-ene, cyclohexyl-1,4-ene, etc. Exemplary arylene linking moietys include, but are not limited to, mono- or bicyclic arylene groups having from 6 to about 14 carbon atoms, e.g. phenyl-1,2-ene, naphthyl-1,6-ene, napthyl-2,7-ene, anthracenyl, etc. Exemplary heterocyclyl groups within the scope of the invention include mono- or bicyclic aryl groups having from about 4 to about 12 carbon atoms and about 1 to about 4 hetero atoms, such as N, O and S, where the cyclic moieties may be partially dehydrogenated. Certain heteroaryl groups that may be mentioned as being within the scope of the invention include: pyrrolidinyl, piperidinyl (e.g. 2,5-piperidinyl, 3,5-piperidinyl), piperazinyl, tetrahydrothiophenyl, tetrahydrofuranyl, tetrahydro quinolinyl, tetrahydro isoquinolinyl, tetrahydroquinazolinyl, tetrahydroquinoxalinyl, etc. Exemplary heteroarylene groups include mono- or bicyclic aryl groups having from about 4 to about 12 carbon atoms and about 1 to about 4 hetero atoms, such as N, O and S. Certain heteroaryl groups that may be mentioned as being within the scope of the invention include: pyridylene (e.g. pyridyl-2,5-ene, pyridyl-3,5-ene), pyrimidinyl, thiophenyl, furanyl, quinolinyl, isoquinolinyl, quinazolinyl, quinoxalinyl, etc.

Although a lot of research has focused on the synthesis of oligoribonucleotides the main RNA synthesis strategies that are presently being used commercially include 5'-O-DMT-2'-O-t-butyldimethylsilyl (TBDMS), 5'-O-DMT-2'-O-[1(2- fluorophenyl)-4-methoxypiperidin4-yl] (FPMP), 2'-O-[(triisopropylsilyl)oxy]methyl (2'-O—CH$_2$—O—Si(iPr)$_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. Such an activator would also be amenable to the present invention. The primary groups being used for commercial RNA synthesis are:

| | |
|---|---|
| TBDMS = | 5'-O-DMT-2'-O-t-butyldimethylsilyl; |
| TOM = | 2'-O-[(triisopropylsilyl)oxy]methyl; |
| DOD/ACE = | 5'-O-bis(trimethylsiloxy)cyclododecyloxysilylether-2'-O-bis(2-acetoxyethoxy)methyl; |
| FPMP = | 5'-O-DMT-2'-O-[1(2-fluorophenyl)-4-methoxypiperidin-4-yl]. |

All of the aforementioned RNA synthesis strategies are amenable to the present invention. Strategies that would be a hybrid of the above e.g. using a 5'-protecting group from one strategy with a 2'-O-protecting from another strategy is also amenable to the present invention.

Targets of the Invention

Targeting an oligomeric compound to a particular nucleic acid molecule, in the context of this invention, can be a multistep process. The process usually begins with the identification of a target nucleic acid whose function is to be modulated. The terms "target nucleic acid" and "nucleic acid target", as used herein, refer to any nucleic acid capable of being targeted including without limitation DNA (a cellular gene), RNA (including pre-mRNA and mRNA or portions thereof) transcribed from such DNA, and also cDNA derived from such RNA. In one embodiment the modulation of expression of a selected gene is associated with a particular disorder or disease state. In another embodiment the target nucleic acid is a nucleic acid molecule from an infectious agent.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid. The terms region, segment, and site can also be used to describe an oligomeric compound of the invention such as for example a gapped oligomeric compound having 3 separate segments.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding a nucleic acid target, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense oligomeric compounds of the present invention.

The open reading frame (ORF) or "coding region," which is known in the art to refer to the region between the translation initiation codon and the translation termination codon, is also a region which may be targeted effectively. Within the context of the present invention, one region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an MRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an MRNA is considered to include the 5' cap structure itself as well as the first 50 nucleotides adjacent to the cap site. It is also suitable to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous MRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also suitable target sites. mRNA transcripts produced via the process of splicing of two (or more) mRNAs from different gene sources are known as "fusion transcripts". It is also known that introns can be effectively targeted using antisense oligomeric compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequences.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also suitable target nucleic acids.

The locations on the target nucleic acid to which the antisense oligomeric compounds hybridize are hereinbelow referred to as "suitable target segments." As used herein the term "suitable target segment" is defined as at least an 8-nucleobase portion of a target region to which an active antisense oligomeric compound is targeted. While not wishing to be bound by theory, it is presently believed that these target segments represent portions of the target nucleic acid which are accessible for hybridization.

Exemplary antisense oligomeric compounds include oligomeric compounds that comprise at least the 8 consecutive nucleobases from the 5'-terminus of a targeted nucleic acid e.g. a cellular gene or mRNA transcribed from the gene (the remaining nucleobases being a consecutive stretch of the same oligonucleotide beginning immediately upstream of the 5'-terminus of the antisense oligomeric compound which is specifically hybridizable to the target nucleic acid and continuing until the oligonucleotide contains from about 8 to about 80 nucleobases). Similarly, antisense oligomeric compounds are represented by oligonucleotide sequences that comprise at least the 8 consecutive nucleobases from the 3'-terminus of one of the illustrative antisense oligomeric compounds (the remaining nucleobases being a consecutive stretch of the same oligonucleotide beginning immediately downstream of the 3'-terminus of the antisense oligomeric compound which is specifically hybridizable to the target nucleic acid and continuing until the oligonucleotide contains from about 8 to about 80 nucleobases). One having skill in the art armed with the antisense oligomeric compounds illustrated herein will be able, without undue experimentation, to identify further antisense oligomeric compounds.

Once one or more target regions, segments or sites have been identified, antisense oligomeric compounds are chosen which are sufficiently complementary to the target, i.e., hybridize sufficiently well and with sufficient specificity, to give the desired effect.

In accordance with one embodiment of the present invention, a series of nucleic acid duplexes comprising the antisense oligomeric compounds of the present invention and their complements can be designed for a specific target or targets. The ends of the strands may be modified by the addition of one or more natural or modified nucleobases to form an overhang. The sense strand of the duplex is then designed and synthesized as the complement of the antisense strand and may also contain modifications or additions to either terminus. For example, in one embodiment, both strands of the duplex would be complementary over the central nucleobases, each having overhangs at one or both termini.

For example, a duplex comprising an antisense oligomeric compound having the sequence CGAGAGGCGGACGG-GACCG (SEQ ID NO:1) and having a two-nucleobase overhang of deoxythymidine (dT) would have the following structure:

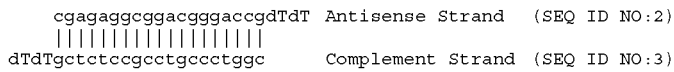

RNA strands of the duplex can be synthesized by methods disclosed herein or purchased from various RNA synthesis companies such as for example Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of the buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA compound is 20 uM. This solution can be stored frozen (−20° C.) and freeze-thawed up to 5 times.

Once prepared, the desired synthetic duplexs are evaluated for their ability to modulate target expression. When cells reach 80% confluency, they are treated with synthetic duplexs comprising at least one oligomeric compound of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired dsRNA compound at a final concentration of 200 nM. After 5 hours of treatment, the medium is replaced with fresh medium. Cells are harvested 16 hours after treatment, at which time RNA is isolated and target reduction measured by RT-PCR.

In a further embodiment, the "suitable target segments" identified herein may be employed in a screen for additional oligomeric compounds that modulate the expression of a target. "Modulators" are those oligomeric compounds that decrease or increase the expression of a nucleic acid molecule encoding a target and which comprise at least an 8-nucleobase portion which is complementary to a suitable target segment. The screening method comprises the steps of contacting a suitable target segment of a nucleic acid molecule encoding a target with one or more candidate modulators, and selecting for one or more candidate modulators which decrease or increase the expression of a nucleic acid molecule encoding a target. Once it is shown that the candidate modulator or modulators are capable of modulating (e.g. either decreasing or increasing) the expression of a nucleic acid molecule encoding a target, the modulator may then be employed in further investigative studies of the function of a target, or for use as a research, diagnostic, or therapeutic agent in accordance with the present invention.

The suitable target segments of the present invention may also be combined with their respective complementary antisense oligomeric compounds of the present invention to form stabilized double stranded (duplexed) oligonucleotides.

Hybridization

In the context of this invention, "hybridization" means hydrogen bonding, which may be Watson-Crick, Hoogsteen or reversed Hoogsteen hydrogen bonding, between the heterocyclic base moieties of complementary nucleosides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense oligomeric compound need not be 100% complementary to that of its target nucleic acid to be specifically hybridizable. An antisense oligomeric compound is specifically hybridizable when binding of the compound to the target DNA or RNA molecule interferes with the normal function of the target DNA or RNA to cause a complete or partial loss of function, and there is a sufficient degree of complementarity to avoid non-specific binding of the antisense oligomeric compound to non-target sequences under conditions in which specific binding is desired, i.e., under physiological conditions in the case of therapeutic treatment, or under conditions in which in vitro or in vivo assays are performed. Moreover, an oligonucleotide may hybridize over one or more segments such that intervening or adjacent segments are not involved in the hybridization event (e.g., a loop structure, mismatch or hairpin structure).

The oligomeric compounds of the present invention comprise at least 70%, at least 75%, at least 80%, at least 85%, at least 90%, at least 95%, at least 99%, or 100% sequence complementarity to a target region within the target nucleic acid sequence to which they are targeted. For example, an antisense oligomeric compound in which 18 of 20 nucleobases of the antisense oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention.

Percent complementarity of an antisense oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some embodiments, homology, sequence identity or complementarity, between the antisense oligomeric compound and target is between about 50% to about 60%. In some embodiments, homology, sequence identity or complementarity, is between about 60% to about 70%. In some embodiments, homology, sequence identity or complementarity, is between about 70% and about 80%. In some embodiments, homology, sequence identity or complementarity, is between about 80% and about 90%. In some embodiments, homology, sequence identity or complementarity, is about 90%, about 92%, about 94%, about 95%, about 96%, about 97%, about 98%, about 99% or about 100%.

Screening and Target Validation

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed in further investigative studies of the function of the peptide, or for use as a research, diagnostic, or therapeutic agent in accordance with the present invention.

The suitable target segments of the present invention may also be combined with their respective complementary antisense oligomeric compounds of the present invention to form stabilized double stranded (duplexed) oligonucleotides. Such double stranded oligonucleotide moieties have been shown in the art to modulate target expression and regulate translation as well as RNA processsing via an antisense mechanism. Moreover, the double stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double stranded moieties have been shown to inhibit the target by the classical hybridization of antisense strand of the duplex to the target, thereby triggering enzymatic degradation of the target (Tijsterman et al., Science, 2002, 295, 694-697).

The oligomeric compounds of the present invention can also be applied in the areas of drug discovery and target validation. The present invention comprehends the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with the oligomeric compounds of the present invention, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype.

Effect of nucleoside modifications on RNAi activity can be evaluated according to existing literature (Elbashir et al., Nature (2001), 411, 494-498; Nishikura et al., Cell (2001), 107, 415-416; and Bass et al., Cell (2000), 101, 235-238.)

Kits, Research Reagents, Diagnostics, and Therapeutics

The oligomeric compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the oligomeric compounds of the present invention, either alone or in combination with other oligomeric compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense oligomeric compounds are compared to control cells or tissues not treated with antisense oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

The oligomeric compounds of the invention are useful for research and diagnostics, in one aspect because they hybridize to nucleic acids encoding proteins. For example, oligonucleotides that are shown to hybridize with such efficiency and under such conditions as disclosed herein as to be effective protein inhibitors will also be effective primers or probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

The specificity and sensitivity of antisense is also harnessed by those of skill in the art for therapeutic uses. Antisense oligomeric compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense oligomeric compounds can be useful therapeutic modalities that can be configured to be useful in treatment regimes for the treatment of cells, tissues and animals, especially humans.

Formulations

As used herein, the term "patient" refers to a mammal that is afflicted with one or more disorders associated with expression or overexpression of one or more genes. It will be understood that the most suitable patient is a human. It is also understood that this invention relates specifically to the inhibition of mammalian expression or overexpression of one or more genes.

It is recognized that one skilled in the art may affect the disorders associated with expression or overexpression of a gene by treating a patient presently afflicted with the disorders with an effective amount of one or more oligomeric compounds or compositions of the present invention. Thus, the terms "treatment" and "treating" are intended to refer to all processes wherein there may be a slowing, interrupting, arresting, controlling, or stopping of the progression of the disorders described herein, but does not necessarily indicate a total elimination of all symptoms.

As used herein, the term "effective amount" or "therapeutically effective amount" of a compound of the present invention refers to an amount that is effective in treating or preventing the disorders described herein.

For therapeutics, a patient, such as a human, suspected of having a disease or disorder which can be treated by modulating the expression of a gene is treated by administering antisense oligomeric compounds in accordance with this invention. The compounds of the invention can be utilized in pharmaceutical compositions by adding an effective amount of an antisense oligomeric compound to a suitable pharmaceutically acceptable diluent or carrier. Use of the antisense oligomeric compounds and methods of the invention may also be useful prophylactically, e.g., to prevent or delay infection, inflammation or tumor formation, for example.

The oligomeric compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents. For oligonucleotides, examples of pharmaceutically acceptable salts and their uses are further described in U.S. Pat. No. 6,287,860, which is incorporated herein in its entirety.

The compositions of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The present invention also includes pharmaceutical compositions and formulations which include the compositions of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Penetration enhancers and their uses are further described in U.S. Pat. No. 6,287,860, which is incorporated herein in its entirety. Surfactants and their uses are further described in U.S. Pat. No. 6,287,860, which is incorporated herein in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. No. 09/108,673 (filed Jul. 1, 1998), Ser. No. 09/315,298 (filed May 20, 1999) and Ser. No. 10/071,822, filed Feb. 8, 2002, each of which is incorporated herein by reference in their entirety.

In another related embodiment, therapeutically effective combination therapies may comprise the use of two or more compositions of the invention wherein the multiple compositions are targeted to a single or multiple nucleic acid targets. Numerous examples of antisense oligomeric compounds are known in the art. Two or more combined compounds may be used together or sequentially.

While the embodiments of the invention have been described with specificity in accordance with certain of the embodiments, the following examples serve only to illustrate the invention and are not intended to limit the same.

Dosing

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, weekly, monthly, or yearly. For double-stranded compounds, the dose must be calculated to account for the increased nucleic acid load of the second strand (as with compounds comprising two separate strands) or the additional nucleic acid length (as with self complementary single strands having double-stranded regions).

EXAMPLE 1

Synthesis of Nucleoside Phosphoramidites

The preparation of nucleoside phosphoramidites is performed following procedures that are extensively illustrated in the art such as but not limited to U.S. Pat. No. 6,426,220 and published PCT WO 02/36743.

EXAMPLE 2

Oligonucleotide and Oligonucleoside Synthesis

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M NH$_4$OAc solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. Nos. 5,256,775 or 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

EXAMPLE 3

Design and Screening of Duplexed Antisense Oligomeric Compounds Directed to a Selected Target In accordance with the present invention, double stranded compositions comprising oligomeric compounds of the present invention can be designed to a particular target. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of the buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense oligomeric compounds are evaluated for their ability to modulate expression of a selected target.

When cells reached 80% confluency, they are treated with duplexed antisense oligomeric compounds of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense oligomeric compound at a final concentration of 200 nM. After 5 hours of treatment, the medium is replaced with fresh medium. Cells are harvested 16 hours after treatment, at which time RNA is isolated and target reduction measured by RT-PCR.

EXAMPLE 4

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32 +/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

EXAMPLE 5

Oligonucleotide Synthesis—96 Well Plate Format

Oligonucleotides can be synthesized via solid phase P(III) phosphoramidite chemistry on an automated synthesizer capable of assembling 96 sequences simultaneously in a 96-well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphorarnidites are purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides are cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

EXAMPLE 6

Oligonucleotide Analysis Using 96-Well Plate Format

The concentration of oligonucleotide in each well is assessed by dilution of samples and UV absorption spectroscopy. The full-length integrity of the individual products is evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

EXAMPLE 7

Cell Culture and Oligonucleotide Treatment

The effect of oligomeric compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR. T-24 cells:

The human transitional cell bladder carcinoma cell line T-24 is obtained from the American Type Culture Collection (ATCC) (Manassas, Va.). T-24 cells are routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells are routinely passaged by trypsinization and dilution when they reached 90% confluence. Cells are seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide. A549 cells:

The human lung carcinoma cell line A549 is obtained from the American Type Culture Collection (ATCC) (Manassas, Va.). A549 cells are routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells are routinely passaged by trypsinization and dilution when they reached 90% confluence. NHDF cells:

Human neonatal dermal fibroblast (NHDF) are obtained from the Clonetics Corporation (Walkersville, Md.). NHDFs are routinely maintained in Fibroblast Growth Medium (Clonetics Corporation, Walkersville, Md.) supplemented as recommended by the supplier. Cells are maintained for up to 10 passages as recommended by the supplier. HEK cells:

Human embryonic keratinocytes (HEK) are obtained from the Clonetics Corporation (Walkersville, Md.). HEKs are routinely maintained in Keratinocyte Growth Medium (Clonetics Corporation, Walkersville, Md.) formulated as recommended by the supplier. Cells are routinely maintained for up to 10 passages as recommended by the supplier.

Treatment with Oligomeric Compounds:

When cells reached 65-75% confluency, they are treated with oligonucleotide. For cells grown in 96-well plates, wells are washed once with 100 μL OPTI-MEM™-1 reduced-serum medium (Invitrogen Corporation, Carlsbad, Calif.) and then treated with 130 μL of OPTI-MEMT™1 containing 3.75 μg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium is replaced with fresh medium. Cells are harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG, SEQ ID NO: 4) which is targeted to human H-ras, or ISIS 18078, (GTGCGCGCGAGCCCGAAATC, SEQ ID NO: 5) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAG-GA, SEQ ID NO: 6, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

EXAMPLE 8

Analysis of Oligonucleotide Inhibition of a Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

EXAMPLE 9

Design of Phenotypic Assays and In Vivo Studies for the Use of a Target Inhibitors Phenotypic Assays Once a target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the geneotype of the cell (measurement of the expression of one or more of the genes of the cell) after treatment is also used as an indicator of the efficacy or potency of the a target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study.

To account for the psychological effects of receiving treatments, volunteers are randomly given placebo or a target inhibitor. Furthermore, to prevent the doctors from being biased in treatments, they are not informed as to whether the medication they are administering is a a target inhibitor or a placebo. Using this randomization approach, each volunteer has the same chance of being given either the new treatment or the placebo.

Volunteers receive either the a target inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding a target or a target protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements.

Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and a target inhibitor treatment. In general, the volunteers treated with placebo have little or no response to treatment, whereas the volunteers treated with the a target inhibitor show positive trends in their disease state or condition index at the conclusion of the study.

EXAMPLE 10

RNA Isolation

Poly(A)+mRNA Isolation

Poly(A)+mRNA is isolated according to Miura et al., (*Clin. Chem.*, 1996, 42, 1758-1764). Other methods for poly (A)+mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVA™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

EXAMPLE 11

Real-Time Quantitative PCR Analysis of a Target mRNA Levels

Quantitation of a target mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa.) is attached to the 5' end of the probe and a quencher dye (e.g., TARRA, obtained from either PE-Applied Biosystems, Foster City, Calif., Operon Technologies Inc., Alameda, Calif. or Integrated DNA Technologies Inc., Coralville, Iowa.) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of MRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 μL PCR cocktail (2.5×PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Probes and are designed to hybridize to a human a target sequence, using published sequence information.

EXAMPLE 12

Northern Blot Analysis of a Target mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio.). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2e400 (Stratagene, Inc, La Jolla, Calif.) and then probed using QUICKHYB™ hybridization solution (Stratagene, La Jolla, Calif.) using manufacturer's recommendations for stringent conditions.

To detect human a target, a human a target specific primer probe set is prepared by PCR To normalize for variations in loading and transfer efficiency membranes are stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

EXAMPLE 13

Inhibition of Human a Target Expression by Oligomeric Compounds

In accordance with the present invention, a series of oligomeric compounds are designed to target different regions of the human target RNA. The oligomeric compounds are analyzed for their effect on human target mRNA levels by quantitative real-time PCR as described in other examples herein. Data are averages from three experiments. The target regions to which these preferred sequences are complementary are herein referred to as "preferred target segments" and are therefore preferred for targeting by oligomeric compounds of the present invention. The sequences represent the reverse complement of the preferred oligomeric compounds.

As these "preferred target segments" have been found by experimentation to be open to, and accessible for, hybridization with the oligomeric compounds of the present invention, one of skill in the art will recognize or be able to ascertain, using no more than routine experimentation, further embodiments of the invention that encompass other oligomeric compounds that specifically hybridize to these preferred target segments and consequently inhibit the expression of a target.

According to the present invention, oligomeric compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

EXAMPLE 14

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

EXAMPLE 15

Representative Cell Lines

MCF-7 Cells

The human breast carcinoma cell line MCF-7 is obtained from the American Type Culture Collection (Manassas, Va.). These cells contain a wild-type p53 gene. MCF-7 cells are routinely cultured in DMEM low glucose (Gibco/Life Technologies, Gaithersburg, Md.) supplemented with 10% fetal calf serum (Gibco/Life Technologies, Gaithersburg, Md.). Cells are routinely passaged by trypsinization and dilution when they reach 90% confluence. Cells are seeded into 96-well plates (Falcon-Primaria #3872) at a density of 7000 cells/well for treatment with the oligomeric compounds of the invention.

HepB3 Cells

The human hepatoma cell line HepB3 (Hep3B2.1-7) is obtained from the American Type Culture Collection (ATCC-ATCC Catalog # HB-8064) (Manassas, Va.). This cell line was initially derived from a hepatocellular carcinoma of an 8-yr-old black male. The cells are epithelial in morphology and are tumorigenic in nude mice. HepB3 cells are routinely cultured in Minimum Essential Medium (MEM) with Earle's Balanced Salt Solution, 2 mM L-glutamine, 1.5 g/L sodium bicarbonate, 0.1 mM nonessential amino acids, 1.0 mM sodium pyruvate (ATCC #20-2003, Manassas, Va.) and with 10% heat-inactivated fetal bovine serum (Gibco/Life Technologies, Gaithersburg, Md.). Cells are routinely passaged by trypsinization and dilution when they reach 90% confluence.

T-24 Cells

The transitional cell bladder carcinoma cell line T-24 is obtained from the American Type Culture Collection (ATCC) (Manassas, Va.). T-24 cells are routinely cultured in complete McCoy's 5 Å basal media (Gibco/Life Technologies, Gaithersburg, Md.) supplemented with 10% fetal calf serum (Gibco/Life Technologies, Gaithersburg, Md.), penicillin 100 units per mL, and streptomycin 100 μg/mL (Gibco/Life Technologies, Gaithersburg, Md.). Cells are routinely passaged by trypsinization and dilution when they reach 90% confluence. Cells are seeded into 96-well plates (Falcon-Primaria #3872) at a density of 7000 cells/well for treatment with the compound of the invention.

A549 Cells

The human lung carcinoma cell line A549 is obtained from the American Type Culture Collection (ATCC) (Manassas, Va.). A549 cells are routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 μg/mL (Gibco/Life Technologies, Gaithersburg, Md.). Cells are routinely passaged by trysinization and dilution when they reach 90% confluence. Cells are seeded into 96-well plates (Falcon-Primaria #3872) at a density of 7000 cells/well for treatment with the compound of the invention.

Primary Mouse Hepatocytes

Primary mouse hepatocytes are prepared from CD-1 mice purchased from Charles River Labs. Primary mouse hepatocytes are routinely cultured in Hepatocyte Attachment Media (Invitrogen Life Technologies, Carlsbad, Calif.) supplemented with 10% Fetal Bovine Serum (Invitrogen Life Technologies, Carlsbad, Calif.), 250 mM dexamethasone (Sigma-Aldrich Corporation, St. Louis, Mo.), 10 nM bovine insulin (Sigma-Aldrich Corporation, St. Louis, Mo.). Cells are seeded into 96-well plates (Falcon-Primaria #353872, BD Biosciences, Bedford, Mass.) at a density of 4000-6000 cells/well for treatment with the oligomeric compounds of the invention.

EXAMPLE 16

Liposome-Mediated Treatment with Oligomeric Compounds of the Invention

When cells reach the desired confluency, they can be treated with the oligomeric compounds of the invention by liposome-mediated transfection. For cells grown in 96-well plates, wells are washed once with 200 μL OPTI-MEM™-1 reduced-serum medium (Gibco BRL) and then treated with 100 μL of OPTI-MEM™-1 containing 2.5 μg/mL LIPOFECTIN™ (Gibco BRL) and the oligomeric compounds of the invention at the desired final concentration. After 4 hours of treatment, the medium is replaced with fresh medium. Cells are harvested 16 hours after treatment with the oligomeric compounds of the invention for target mRNA expression analysis by real-time PCR.

EXAMPLE 17

Electroporation-Mediated Treatment with Oligomeric Compounds of the Invention When the cells reach the desired confluency, they can be treated with the oligomeric compounds of the invention by electorporation. Cells are electroporated in the presence of the desired concentration of an oligomeric compound of the invention in 1 mm cuvettes at a density of $1 \times 10^7$ cells/mL, a voltage of 75V and a pulse length of 6 ms. Following the delivery of the electrical pulse, cells are replated for 16 to 24 hours. Cells are then harvested for target MRNA expression analysis by real-time PCR.

EXAMPLE 18

Apoptosis Assay

Caspase-3 activity is evaluated with an fluorometric HTS Caspase-3 assay (Oncogene Research Products, San Diego, Calif.) that detects cleavage after aspartate residues in the peptide sequence (DEVD). The DEVD substrate is labeled with a fluorescent molecule, which exhibits a blue to green shift in fluorescence upon cleavage. Active caspase-3 in treated cells is measured by this assay according to the manufacturer's instructions. Following treatment with the oligomeric compounds of the invention, 50 μL of assay buffer is added to each well, followed by addition 20 μL of the caspase-3 fluorescent substrate conjugate. Data are obtained in triplicate. Fluorescence in wells is immediately detected (excitation/emission 400/505 nm) using a fluorescent plate reader (SpectraMAX GeminiXS, Molecular Devices, Sunnyvale, Calif.). The plate is covered and incubated at 37° C. for an additional three hours, after which the fluorescence is again measured (excitation/emission 400/505 nm). The value at time zero is subtracted from the measurement obtained at 3 hours. The measurement obtained from the untreated control cells is designated as 100% activity.

EXAMPLE 19

Cell Proliferation and Viability Assay

Cell viability and proliferation are measured using the CyQuant Cell Proliferation Assay Kit (Molecular Probes, Eugene, Oreg.) utilizing the CyQuant GR green fluorescent dye which exhibits strong fluorescence enhancement when bound to cellular nucleic acids. The assay is performed according to the manufacturer's instructions. After the treatment with one or more oligomeric compounds of the invention, the microplate is gently inverted to remove the medium from the wells, which are each washed once with 200 μL of phosphate-buffered saline. Plates are frozen at −70° C. and then thawed. A volume of 200 μL of the CyQUANT GR dye/cell-lysis buffer is added to each well. The microplate is incubated for 5 minutes at room temperature, protected from light. Data are obtained in triplicate. Fluorescence in wells is immediately detected (excitation/emission 480/520 nm) using a fluorescent plate reader (SpectraMAX GeminiXS, Molecular Devices, Sunnyvale, Calif.). The measurement obtained from the untreated control cells is designated as 100% activity.

EXAMPLE 20

Leptin-Deficient Mice: A Model of Obesity and Diabetes (ob/ob Mice)

Leptin is a hormone produced by fat that regulates appetite. Deficiencies in this hormone in both humans and non-human animals leads to obesity. ob/ob mice have a mutation in the leptin gene which results in obesity and hyperglycemia. As such, these mice are a useful model for the investigation of obesity and diabetes and treatments designed to treat these conditions. ob/ob mice have higher circulating levels of insulin and are less hyperglycemic than db/db mice, which harbor a mutation in the leptin receptor. In accordance with the present invention, the oligomeric compounds of the invention are tested in the ob/ob model of obesity and diabetes.

Seven-week old male C57Bl/6J-Lepr ob/ob mice (Jackson Laboratory, Bar Harbor, Me.) are fed a diet with a fat content of 10-15% and are subcutaneously injected with the oligomeric compounds of the invention or a control compound at a dose of 25 mg/kg two times per week for 4 weeks. Saline-injected animals, leptin wildtype littermates (i.e. lean littermates) and ob/ob mice fed a standard rodent diet serve as controls. After the treatment period, mice are sacrificed and target levels are evaluated in liver, brown adipose tissue (BAT) and white adipose tissue (WAT). RNA isolation and target mRNA expression level quantitation are performed as described by other examples herein.

To assess the physiological effects resulting from inhibition of target MRNA, the ob/ob mice are further evaluated at the end of the treatment period for serum lipids, serum free fatty acids, serum cholesterol (CHOL), liver triglycerides, fat tissue triglycerides and liver enzyme levels. Hepatic steatosis, or clearing of lipids from the liver, is assessed by measuring the liver triglyceride content. Hepatic steatosis is assessed by routine histological analysis of frozen liver tissue sections stained with oil red O stain, which is commonly used to visualize lipid deposits, and counterstained with hematoxylin and eosin, to visualize nuclei and cytoplasm, respectively.

The effects of target inhibition on glucose and insulin metabolism are evaluated in the ob/ob mice treated with the oligomeric compounds of the invention. Plasma glucose is measured at the start of the treatment and after 2 weeks and 4 weeks of treatment. Plasma insulin is similarly measured at the beginning of the treatment, and following at 2 weeks and at 4 weeks of treatment. Glucose and insulin tolerance tests are also administered in fed and fasted mice. Mice receive intraperitoneal injections of either glucose or insulin, and the blood glucose and insulin levels are measured before the insulin or glucose challenge and at 15, 20 or 30 minute intervals for up to 3 hours.

To assess the metabolic rate of ob/ob mice treated with the oligomeric compounds of the invention, the respiratory quotient and oxygen consumption of the mice are also measured.

The ob/ob mice that received treatment are further evaluated at the end of the treatment period for the effects of target inhibition on the expression genes that participate in lipid metabolism, cholesterol biosynthesis, fatty acid oxidation, fatty acid storage, gluconeogenesis and glucose metabolism. These genes include, but are not limited to, HMG-CoA reductase, acetyl-CoA carboxylase 1 and acetyl-CoA carboxylase 2, carnitine palmitoyltransferase I and glycogen phosphorylase, glucose-6-phosphatase and phosphoenolpyruvate carboxykinase 1, lipoprotein lipase and hormone sensitive lipase. mRNA levels in liver and white and brown adipose tissue are quantitated by real-time PCR as described in other examples herein, employing primer-probe sets that are generated using published sequences of each gene of interest.

EXAMPLE 21

Leptin Receptor-Deficient Mice: A Model of Obesity and Diabetes (db/db Mice)

Leptin is a hormone produced by fat that regulates appetite. Deficiencies in this hormone in both humans and non-human animals leads to obesity. db/db mice have a mutation in the leptin receptor gene which results in obesity and hyperglycemia. As such, these mice are a useful model for the investigation of obesity and diabetes and treatments designed to treat these conditions. db/db mice, which have lower circulating levels of insulin and are more hyperglycemic than ob/ob mice which harbor a mutation in the leptin gene, are often used as a rodent model of type 2 diabetes. In accordance with the present invention, oligomeric compounds of the present invention are tested in the db/db model of obesity and diabetes.

Seven-week old male C57Bl/6J-Lepr db/db mice (Jackson Laboratory, Bar Harbor, Me.) are fed a diet with a fat content of 15-20% and are subcutaneously injected with one or more of the oligomeric compounds of the invention or a control compound at a dose of 25 mg/kg two times per week for 4 weeks. Saline-injected animals, leptin receptor wildtype littermates (i.e. lean littermates) and db/db mice fed a standard rodent diet serve as controls. After the treatment period, mice are sacrificed and target levels are evaluated in liver, brown adipose tissue (BAT) and white adipose tissue (WAT). RNA isolation and target mRNA expression level quantitation are performed as described by other examples herein.

After the treatment period, mice are sacrificed and target levels are evaluated in liver, brown adipose tissue (BAT) and white adipose tissue (WAT). RNA isolation and target mRNA expression level quantitation are performed as described by other examples herein.

To assess the physiological effects resulting from inhibition of target mRNA, the db/db mice that receive treatment are further evaluated at the end of the treatment period for serum lipids, serum free fatty acids, serum cholesterol (CHOL), liver triglycerides, fat tissue triglycerides and liver enzyme levels. Hepatic steatosis, or clearing of lipids from the liver, is assessed by measuring the liver triglyceride content. Hepatic steatosis is also assessed by routine histological analysis of frozen liver tissue sections stained with oil red O stain, which is commonly used to visualize lipid deposits, and counterstained with hematoxylin and eosin, to visualize nuclei and cytoplasm, respectively.

The effects of target inhibition on glucose and insulin metabolism are also evaluated in the db/db mice treated with the oligomeric compounds of the invention. Plasma glucose is measured at the start of the treatment and after 2 weeks and 4 weeks of treatment. Plasma insulin is similarly measured at the beginning of the treatment, and following 2 weeks and 4 weeks of treatment. Glucose and insulin tolerance tests are also administered in fed and fasted mice. Mice receive intraperitoneal injections of either glucose or insulin, and the blood glucose levels are measured before the insulin or glucose challenge and 15, 30, 60, 90 and 120 minutes following the injection. To assess the metabolic rate of db/db mice treated with the oligomeric compounds of the invention, the respiratory quotient and oxygen consumption of the mice is also measured.

The db/db mice that receive treatment are further evaluated at the end of the treatment period for the effects of target inhibition on the expression genes that participate in lipid metabolism, cholesterol biosynthesis, fatty acid oxidation, fatty acid storage, gluconeogenesis and glucose metabolism. These genes include, but are not limited to, HMG-CoA reductase, acetyl-CoA carboxylase 1 and acetyl-CoA carboxylase 2, carnitine palmitoyltransferase I and glycogen phosphorylase, glucose-6-phosphatase and phosphoenolpyruvate carboxykinase 1, lipoprotein lipase and hormone sensitive lipase. mRNA levels in liver and white and brown adipose tissue are quantitated by real-time PCR as described in other examples herein, employing primer-probe sets that are generated using published sequences of each gene of interest.

EXAMPLE 22

Lean Mice on a Standard Rodent Diet

C57Bl/6 mice are maintained on a standard rodent diet and are used as control (lean) animals. In a further embodiment of the present invention, the oligomeric compounds of the invention are tested in normal, lean animals. Seven-week old male C57Bl/6 mice are fed a diet with a fat content of 4% and are subcutaneously injected with one or more of the oligomeric compounds of the invention or control compounds at a dose of 25 mg/kg two times per week for 4 weeks. Saline-injected animals serve as a control. After the treatment period, mice are sacrificed and target levels are evaluated in liver, brown adipose tissue (BAT) and white adipose tissue (WAT). RNA isolation and target mRNA expression level quantitation are performed as described by other examples herein.

After the treatment period, mice are sacrificed and target levels are evaluated in liver, brown adipose tissue (BAT) and white adipose tissue (WAT). RNA isolation and target mRNA expression level quantitation are performed as described by other examples herein.

To assess the physiological effects resulting from inhibition of target mRNA, the lean mice that receive treatment are further evaluated at the end of the treatment period for serum lipids, serum free fatty acids, serum cholesterol (CHOL), liver triglycerides, fat tissue triglycerides and liver enzyme levels. Hepatic steatosis, or clearing of lipids from the liver, is assessed by measuring the liver triglyceride content. Hepatic steatosis is also assessed by routine histological analysis of frozen liver tissue sections stained with oil red O stain, which is commonly used to visualize lipid deposits, and counterstained with hematoxylin and eosin, to visualize nuclei and cytoplasm, respectively.

The effects of target inhibition on glucose and insulin metabolism are also evaluated in the lean mice treated with the oligomeric compounds of the invention. Plasma glucose is measured at the start of the treatment and after 2 weeks and 4 weeks of treatment. Plasma insulin is similarly measured at the beginning of the treatment, and following 2 weeks and 4 weeks of treatment. Glucose and insulin tolerance tests are also administered in fed and fasted mice. Mice receive intraperitoneal injections of either glucose or insulin, and the blood glucose levels are measured before the insulin or glucose challenge and 15, 30, 60, 90 and 120 minutes following the injection. To assess the metabolic rate of lean mice treated with the oligomeric compounds of the invention, the respiratory quotient and oxygen consumption of the mice is also measured.

The lean mice that received treatment are further evaluated at the end of the treatment period for the effects of target inhibition on the expression genes that participate in lipid metabolism, cholesterol biosynthesis, fatty acid oxidation, fatty acid storage, gluconeogenesis and glucose metabolism. These genes include, but are not limited to, HMG-CoA reductase, acetyl-CoA carboxylase 1 and acetyl-CoA carboxylase 2, carnitine palmitoyltransferase I and glycogen phosphorylase, glucose-6-phosphatase and phosphoenolpyruvate carboxykinase 1, lipoprotein lipase and hormone sensitive lipase. MRNA levels in liver and white and brown adipose tissue are quantitated by real-time PCR as described in other examples herein, employing primer-probe sets that are generated using published sequences of each gene of interest.

EXAMPLE 23

Modulation of Human Survivin Expression by Double Stranded RNA (dsRNA)

In accordance with the present invention, a series of double stranded oligomeric compounds comprising the antisense compounds of the present invention and their complements thereof, were designed to target survivin mRNA. The oligomeric compounds were evaluated in HeLa cells. Culture methods used for HeLa cells are found, for example, at http://www.atcc.org.

For cells grown in 96-well plates, wells were washed once with 200 µL OPTI-MEM-1™ reduced-serum medium (Gibco BRL) and then treated with 130 µL of OPTI-MEM-1™ containing 12 µg/mL LIPOFECTIN™ (Gibco BRL) and the desired dsRNA at a final concentration of 25 nM. After 5 hours of treatment, the medium was replaced with fresh medium. Cells were harvested 16 hours after dsRNA treatment, at which time RNA was isolated and target reduction measured by RT-PCR.

Prior to treatment of the HeLa cells, the dsRNA oligomers were generated by annealing the antisense and sense strands according to the method outlined herein and known to those skilled in the art.

EXAMPLE 24

Design and Screening of Duplexed Antisense Compounds Targeting Survivin

In accordance with the present invention, a series of nucleic acid duplexes comprising the antisense compounds of the present invention and their complements can be designed to target survivin. The nucleobase sequence of the antisense strand of the duplex comprises at least a portion of an oligonucleotide to survivin as described herein. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 1) and having a two-nucleobase overhang of deoxythymidine (dT) would have the following structure:

|  |  | SEQ ID NO. |
|---|---|---|
| cgagaggcggacgggaccgdTdT<br>\|\|\|\|\|\|\|\|\|\|\|\|\|\|\|\|\|\|\|<br>dTdTgctctccgcctgccctggc | Antisense Strand<br><br>Complement Strand | 2<br><br>3 |

In another embodiment, a duplex comprising an antisense strand having the same sequence CGAGAGGCGGACGG-GACCG (SEQ ID NO: 1) may be prepared with blunt ends (no single stranded overhang) as shown:

|  |  | SEQ ID NO. |
|---|---|---|
| cgagaggcggacgggaccg<br>\|\|\|\|\|\|\|\|\|\|\|\|\|\|\|\|\|\|\|<br>gctctccgcctgccctggc | Antisense Strand<br><br>Complement Strand | 1<br><br>7 |

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate survivin expression according to the protocols described herein.

EXAMPLE 25

Alternating 2'-O-Methyl/2'-F siRNA's Targeting PTEN in T-24 Cells

A dose response was performed in the PTEN system to look at positional effects of alternating 2'-O-Methyl/2'-F siRNA's.

| SEQ ID NO/<br>ISIS NO | SEQUENCE (Bold = 2'-F,<br>Underlined = 2'-OCH$_3$) |  |
|---|---|---|
| 8/308746<br>9/303912 | 5'-P-AAG UAA GGA CCA GAG AC AAA-3'<br>3'-UUC AUU CCU GGU CUC UGU UU-P-5' | (PO, S, RNA)<br>(PS, AS, RNA) |
| 8/340573<br>9/340569 | 5'-PO-AAG UAA GGA CCA GAG ACA AA-3'<br>3'-UUC AUU CCU GGU CUC UGU UU-P-5' | (PO,S)<br>(PO, AS) |
| 8/340574<br>9/340569 | 5'-PO-AAG UAA GGA CCA GAG ACA AA-3'<br>3'-UUC AUU CCU GGU CUC UGU UU-P-5' | (PO,S)<br>(PO, AS) |
| 8/308746<br>9/340569 | 5'-PO-AAG UAA GGA CCA GAG ACA AA-3'<br>3'-UUC AUU CCU GGU CUC UGU UU-P-5' | (PO, AS, RNA)<br>(PO, AS) |
| 8/340573<br>9/340570 | 5'-PO-AAG UAA GGA CCA GAG ACA AA-3'<br>3'-UUC AUU CCU GGU CUC UGU UU-P-5' | (PO, S)<br>(PS, AS) |
| 8/340574<br>9/340570 | 5'-PO-AAG UAA GGA CCA GAG ACA AA-3'<br>3'-UUC AUU CCU GGU CUC UGU UU-P-5' | (PO,S)<br>(PS, AS) |
| 8/308746<br>9/340570 | 5'-PO-AAG UAA GGA CCA GAG ACA AA-3'<br>3'-UUC AUU CCU GGU CUC UGU UU-P-5' | (PO, AS, RNA)<br>(PS, AS) |

Underlined nucleosides are 2'-OCH$_3$ modified nucleosides, bold are 2'-F modified nucleosides, PO and PS are phosphodiester and phosphorothioate respectively, 5'-P is 5'-phosphate, and $^m$C's are 5-methyl cytidines.

The above siRNA constructs were assayed to determine the effects of the full alternating 2'-O-methyl/2'-F antisense strands (PO or PS) where the 5'-terminus of the antisense strands are 2'-F modified nucleosides with the remaining positions alternating. The sense strands were prepared with the positioning of the modified nucleosides in both orientations such that for each siRNA tested with 2'-O-methyl modified nucleosides beginning at the the 3'-terminus of the sense strand another identical siRNA was prepared with 2'-F modified nucleosides beginning at the the 3'-terminus of the sense strand. Another way to describe the differences between these two siRNA's is that the register of the sense strand is in both possible orientations with the register of the antisense strand being held constant in one orientation.

The activities are listed below:

| siRNA Construct | Activity (% untreated control 150 nM) | Sense | Antisense |
|---|---|---|---|
| 308746/303912 | 28% | PO unmodified RNA | PS unmodified RNA |
| 340574/340569 | 46% | PO (2'-F, 3'-0) | PO (2'-F, 5'-0) |
| 340574/340570 | 62% | PO (2'-F, 3'-0) | PS (2'-F, 5'-0) |
| 340573/340569 | 84% | PO (2'-O-methyl, 3'-0) | PO (2'-F, 5'-0) |
| 340573/340570 | 23% | PO (2'-O-methyl, 3'-0) | PS (2'-F, 5'-0) |
| 308746/340569 | 23% | PO unmodified RNA | PO (2'-F, 5'-0) |
| 308746/340570 | 38% | PO unmodified RNA | PS (2'-F, 5'-0) |

Within the alternating motif for this assay the antisense strands were prepared beginning with a 2'-F group at the 5'-terminal nucleoside. The sense strands were prepared with the alternating motif beginning at the 3'-terminal nucleoside with either the 2'-F (2'-F, 3'-0) or the 2'-O-methyl (2'-O-methyl, 3'-0). The siRNA constructs were prepared with the internucleoside linkages for the sense strand as full phosphodiester and the internucleoside linkages for the antisense strands as either full phosphodiester or phosphorothioate.

EXAMPLE 26

Alternating 2'-O-Methyl/2'-F siRNA's Targeting PTEN in T-24 Cells

A dose response was performed in the PTEN system to look at positional effects of alternating 2'-O-Methyl/2'-F siRNA's.

```
SEQ ID NO/   SEQUENCE (Bold = 2'-F,
ISIS NO      Underlined = 2'-OCH₃)

8/308746     5'-P-AAG UAA GGA CCA GAG AC AAA-3'    (PO, S, RNA)
10/303912    5'-P-UU UGU CUC UGG UCC UUA CUU-3'    (AS, PS, RNA)

8/340573     5'-P-AAG UAA GGA CCA GAG ACA AA-3'    (PO, S)
10/340571    5'-P-UUU GUC UCU GGU CCU UAC UU-3'    (AS, PO)

8/340574     5'-P-AAG UAA GGA CCA GAG ACA AA-3'    (S, PO)
10/340571    5'-P-UUU GUC UCU GGU CCU UAC UU-3'    (AS, PO)

8/308746     5'-P-AAG UAA GGA CCA GAG AC AAA-3'    (PO, S, RNA)
10/340571    5'-P-UUU GUC UCU GGU CCU UAC UU-3'    (AS, PO)

8/340573     5'-P-AAG UAA GGA CCA GAG ACA AA-3'    (PO, S)
10/340572    5'-P-UUU GUC UCU GGU CCU UAC UU-3'    (AS, PS)

8/340574     5'-P-AAG UAA GGA CCA GAG ACA AA-3'    (S, PO)
10/340572    5'-P-UUU GUC UCU GGU CCU UAC UU-3'    (AS, PS)

8/308746     5'-P-AAG UAA GGA CCA GAG AC AAA-3'    (PO, S, RNA)
10/340572    5'-P-UUU GUC UCU GGU CCU UAC UU-3'    (AS, PS)
```

Underlined nucleosides are 2'-OCH₃ modified nucleosides, bold are 2'-F modified nucleosides, PO and PS are phosphodiester and phosphorothioate respectively, 5'-P is 5'-phosphate.

The above siRNA constructs were assayed to determine the effects of the full alternating 2'-O-methyl/2'-F antisense strands (PO or PS) where the 5'-terminus of the antisense strands are 2'-O-methyl modified nucleosides with the remaining positions alternating. The sense strands were prepared with the positioning of the modified nucleosides in both orientations such that for each siRNA tested with 2'-O-methyl modified nucleosides beginning at the the 3'-terminus of the sense strand another identical siRNA was prepared with 2'-F modified nucleosides beginning at the 3'-terminus of the sense strand. Another way to describe the differences between these two siRNA's is that the register of the sense strand is in both possible orientations with the register of the antisense strand being held constant in one orientation.

The activities are listed below

| siRNA Construct | Activity (% untreated control 150 nM) | Sense | Antisense |
|---|---|---|---|
| 308746/303912 | 27% | PO unmodified RNA | PS unmodified RNA |
| 340574/340571 | 112% | PO (2'-F, 3'-end) | PO (2'-O-methyl, 5'-end) |
| 340574/340572 | 81% | PO (2'-F, 3'-end) | PS (2'-O-methyl, 5'-end) |
| 340573/340571 | 40% | PO (2'-O-methyl, 3'-end) | PO (2'-O-methyl, 5'-end) |
| 340573/340572 | 71% | PO (2'-O-methyl, 3'-end) | PS (2'-O-methyl, 5'-end) |
| 308746/340571 | 46% | PO unmodified RNA | PO (2'-O-methyl, 5'-end) |
| 308746/340572 | 44% | PO unmodified RNA | PS (2'-O-methyl, 5'-end) |

Within the alternating motif for this assay the antisense strands were prepared beginning with a 2'-F group at the 5'-terminal nucleoside. The sense strands were prepared with the alternating motif beginning at the 3'-terminal nucleoside with either the 2'-F (2'-F, 3'-0) or the 2'-O-methyl (2'-O-methyl, 3'-0). The siRNA constructs were prepared with the internucleoside linkages for the sense strand as full phosphodiester and the internucleoside linkages for the antisense strands as either full phosphodiester or phosphorothioate.

EXAMPLE 27

Double Stranded Alternating Constructs Targeted to PTEN

A number of double stranded constructs were also assayed in HeLa cells. The constructs and activities are shown below:

| SEQ ID NO/ ISIS NO | SEQUENCES 5'-3' | |
|---|---|---|
| 10/303912 | 5'-P-UU UGU CUC UGG UCC UUA CUU-3' | (AS, PS) |
| 8/308746 | 5'-P-AAG UAA GGA CCA GAG ACA AA-3' | (S, PO) |
| 10/340569 | 5'-P-UUU GUC UCU GGU CCU UAC UU-3' | (AS PO) |
| 10/340570 | 5'-P-UUU GUC UCU GGU CCU UAC UU-3' | (AS, PS) |
| 10/340571 | 5'-P-UUU GUC UCU GGU CCU UAC UU-3' | (AS, PO) |
| 10/340572 | 5'-P-UUU GUC UCU GGU CCU UAC UU-3' | (AS, PS) |
| 8/340573 | 5'-P-AAG UAA GGA CCA GAG ACA AA-3' | (S, PO) |
| 8/340574 | 5'-P-AAG UAA GGA CCA GAG ACA AA-3' | (S, PO) |

Underlined nucleosides are 2'-OCH$_3$ modified nucleosides, bold are 2'-F modified nucleosides, PO and PS are phosphodiester and phosphorothioate respectively, 5'-P is 5'-phosphate.

The particular constructs and their activities are shown below:

| Double stranded construct | | Activity | |
|---|---|---|---|
| Antisense | Sense | % UTC (dose; nM) | IC50 (nM) |
| 303912 | 308746 | 24 (100) | 2 |
| 340569 | 340573 | 67 (15) | |
| 340569 | 340574 | 35 (15) | 4 |
| 340569 | 308746 | 19 (15) | 0.2 |
| 340570 | 340573 | 25 (15) | 3 |
| 340570 | 340574 | 77 (15) | 92 |
| 340570 | 308746 | 52 (15) | 23 |
| 340571 | 340573 | 32 (15) | 4 |
| 340571 | 340574 | 84 (15) | |
| 340571 | 308746 | 38 (15) | 4 |
| 340572 | 340573 | 64 (15) | |
| 340572 | 340574 | 71 (15) | |
| 340572 | 308746 | 51 (15) | 0.7. |

EXAMPLE 28

Reduction of endogenous PTEN mRNA in HeLa cells by 20-basepair siRNA containing 2'-F and 2'-OMe modifications is shown in this example. HeLa cells were transfected with siRNA in the presence of lipofectin and treated for 16 hours prior to lysis and analysis by RT-PCR. Maximum % reduction is the amount of mRNA reduction compared to untreated control cells at the highest concentration (150 nM), with IC50 indicating the interpolated concentration at which 50% reduction is achieved. The notation "5'—P—" indicates the presence of a 5'-phosphate. Bold nucleosides have 2'-F substituents. Nucleosides with a "m" subscript have 2'-OMe substituents. Otherwise the nuclosides have a 2'-OH substituent. The constructs have phosphodiester linkages unless otherwise listed to the side in brackets.

| SEQ ID | siRNA | |
|---|---|---|
| 8/308746 | 5'-P-AAG UAA GGA CCA GAG ACA AA-3' | (S, PO) |
| 10/303912 | 5'-P-UU UGU CUC UGG UCC UUA CUU-3' | (AS, PS) |
| 8/308746 | 5'-P-AAG UAA GGA CCA GAG ACA AA-3' | (S, PO) |
| 10/340570 | 5'-P-UUU GUC UCU GGU CCU UAC UU-3' | (AS, PS) |
| 8/308746 | 5'-P-AAG UAA GGA CCA GAG ACA AA-3' | (S, PO) |
| 10/340569 | 5'-P-UUU GUC UCU GGU CCU UAC UU-3' | (AS, PO) |
| 8/340574 | 5'-P-AAG UAA GGA CCA GAG ACA AA-3' | (S, PO) |
| 10/340569 | 5'-P-UUU GUC UCU GGU CCU UAC UU-3' | (AS, PO) |
| 8/340574 | 5'-P-AAG UAA GGA CCA GAG ACA AA-3' | (S, PO) |
| 10/340570 | 5'-P-UUU GUC UCU GGU CCU UAC UU-3' | (AS, PS) |
| 8/340573 | 5'-P-AAG UAA GGA CCA GAG ACA AA-3' | (S, PO) |
| 10/340569 | 5'-P-UUU GUC UCU GGU CCU UAC UU-3' | (AS, PO) |
| 8/340573 | 5'-P-AAG UAA GGA CCA GAG ACA AA-3' | (S, PO) |
| 10/340570 | 5'-P-UUU GUC UCU GGU CCU UAC UU-3' | (AS, PS) |
| 8/308746 | 5'-P-AAG UAA GGA CCA GAG ACA AA-3' | (S, PO) |
| 10/340569 | 5'-P-UUU GUC UCU GGU CCU UAC UU-3' | (AS, PO) |
| 8/308746 | 5'-P-AAG UAA GGA CCA GAG ACA AA-3' | (S, PO) |
| 10/340572 | 5'-P-UUU GUC UCU GGU CCU UAC UU-3' | (AS, PS) |
| 8/340573 | 5'-P-AAG UAA GGA CCA GAG ACA AA-3' | (S, PO) |
| 10/340571 | 5'-P-UUU GUC UCU GGU CCU UAC UU-3' | (AS, PO) |
| 8/340573 | 5'-P-AAG UAA GGA CCA GAG ACA AA-3' | (S, PO) |
| 10/340572 | 5'-P-UUU GUC UCU GGU CCU UAC UU-3' | (AS, PS) |
| 8/340574 | 5'-P-AAG UAA GGA CCA GAG ACA AA-3' | (S, PO) |
| 10/340569 | 5'-P-UUU GUC UCU GGU CCU UAC UU-3' | (AS, PO) |
| 8/340574 | 5'-P-AAG UAA GGA CCA GAG ACA AA-3' | (S, PO) |
| 10/340572 | 5'-P-UUU GUC UCU GGU CCU UAC UU-3' | (AS, PS) |

| Double stranded construct | | Activity | |
|---|---|---|---|
| Antisense | Sense | IC50 (nM) | Max Red |
| 13/308746 | 12/303912 | 1.5 | 86 |
| 13/308746 | 13/340570 | 0.18 | 87 |
| 13/308746 | 11/340569 | 23.4 | 66 |
| 12/340574 | 11/340569 | 3.8 | 80 |
| 12/340574 | 13/340570 | 92 | 59 |
| 10/340573 | 11/340569 | 192 | 48 |

| Double stranded construct | | Activity | |
|---|---|---|---|
| Antisense | Sense | IC50 (nM) | Max Red |
| 10/340573 | 13/340570 | 3.4 | 84 |
| 13/308746 | 11/340569 | 3.8 | 70 |
| 13/308746 | 15/340572 | 53.2 | 52 |
| 10/340573 | 14/340571 | 3.5 | 82 |
| 10/340573 | 15/340572 | 13 | 27 |
| 12/340574 | 11/340569 | n.d. | 27 |
| 12/340574 | 15/340572 | n.d. | 32. |

EXAMPLE 29

Reduction of endogenous PTEN mRNA in HeLa cells by 19-basepair siRNAs containing 2'-F and 2'-OMe modifications is shown in this example. HeLa cells were transfected with siRNA in the presence of lipofectin and treated for 16 hours prior to lysis and analysis by RT-PCR. Maximum % reduction is the amount of mRNA reduction compared to untreated control cells at the highest concentration (150 nM), with IC50 indicating the interpolated concentration at which 50% reduction is achieved. The notation "5'—P—" indicates the presence of a 5'-phosphate. Bold nucleosides have 2'-F substituents. Nucleosides with a "m" subscript have 2'-OMe substituents. Otherwise the nucleosides have a 2'-OH substituent. The constructs have phosphodiester linkages unless underlined. Underlined nucleosides have phosphorthioate linkages.

```
SEQ ID NO  SEQUENCES 5'-3'

8          5'-AAG UAA GGA CCA GAG ACA AA-3'      (S,
                                                  PO)

10         5'-P-UU UGU CUC UGG UCC UUA CUU-3'    (AS,
                                                  PO)

8          5'-AAG UAA GGA CCA GAG ACA AA-3'      (S,
                                                  PO)

10/340571  5'-P-UUU GUC UCU GGU CCU UAC UU-3'    (AS,
                                                  PO)

8          5'-AAG UAA GGA CCA GAG ACA AA-3'      (S,
                                                  PO)

10/340572  5'-P-UUU GUC UCU GGU CCU UAC UU-3'    (AS,
                                                  PO)

11         5'-GGG UAA AUA CAU UCU ACA U-3'       (S,
                                                  PO)

12         5'-AUG UAG AAU GUA UUU ACC C-3'       (AS,
                                                  PO)

11         5'-GGG UAA AUA CAU UCU ACA U-3'       (S,
                                                  PO)

12         5'-AUG UAG AAU GUA UUU ACC C-3'       (AS,
                                                  PO)

11         5'-GGG UAA AUA CAU UCU ACA U-3'       (S,
                                                  PO)

12         5'-AUG UAG AAU GUA UUU ACC C-3'       (AS,
                                                  PO)
```

| Double stranded construct | | Activity | |
|---|---|---|---|
| Antisense | Sense | IC50 (nM) | Max Red |
| 16 | 17 | 0.55 | 74 |
| 16 | 14 | 0.66 | 74 |
| 18 | 15 | 0.38 | 81 |
| 19 | 20 | 7.4 | 58 |
| 19 | 21 | 0.29 | 80 |
| 22 | 21 | 0.03 | 88. |

EXAMPLE 30

Additional Alternating Sequences

The following sequences were prepared and assayed for activity as listed below. The notation "5'—P—" indicates the presence of a 5'-phosphate. Bold nucleosides have 2'-F substituents. Nucleosides with a "m" subscript have 2'-OMe substituents. Otherwise the nucleosides have a 2'-OH substituent. The constructs have phosphodiester linkages unless otherwise listed to the side in brackets.

```
Alternating 2'-OCH3/2'-F as/s 2'-OCH3/2'-F (5'-3')
10 (as)/340569   UUUGUCUCUGGUCCUUACUU 8 (s)/340574     AAGUAAGGACCAGAGACAAA 10 (as)/340571   UUUGUCUCUGGUCCUUACUU 8 (s)/340573     AAGUAAGGACCAGAGACAAA 13 (as)/352820   UUGUCUCUGGUCCUUACUU 14 (s)/352821    AAGUAAGGACCAGAGACAA 15 (as)/351827   UGUCAUAUUCCUGGAUCCU 16 (s)/351828    AGGAUCCAGGAAUAUGACA 17 (as)/351829   UCCUGGAUCCUUCACCAAU 18 (s)/351830    AUUGGUGAAGGAUCCAGGA 19 (as)/351831   UCUUAUCACCUUUAGCUCU 20 (s)/351832    AGAGCUAAAGGUGAUAAGA 21 (as)/351833   AUACUCAGAAGGUGUCUUC 22 (s)/351834    GAAGACACCUUCUGAGUAU 23 (as)/355713   UUUGAAAAUGUUGAUCUCC 24 (s)/355714    GGAGAUCAACAUUUUCAAA Alternating 2'-OCH3/2'-F full P=S as/s 2'-
OCH3/2'-F
10 (as)/340570   UUUGUCUCUGGUCCUUACUU (full P=S)

8 (s)/340573     AAGUAAGGACCAGAGACAAA (full P=O)
```

The alternating 2'-F/2'OCH₃ constructs were tested in accordance with the assays described herein. Cell line 20 is HeLa. Cell line 160 is U-87 MG. Cell line 243 is MH-S. Cells are available from commercial sources. For example, HeLa cells can be obtained from American Type Culture Collection, Manassas Va. Culture methods used for HeLa cells are available from the ATCC and may be found, for example, at http://www.atcc.org. For cells grown in 96-well plates, wells were washed once with 200 μL OPTI-MEM-1 reduced-serum medium (Gibco BRL) and then treated with 130 μL of OPTI-MEM-1 containing 12 μg/mL LIPOFECTIN™ (Gibco BRL) and the dsRNA at the desired concentration. After 5 hours of treatment, the medium was replaced with fresh medium. Cells were harvested 16 hours after dsRNA treatment, at which time RNA was isolated and target reduction measured by RT-PCR as described in previous examples.

| Construct | Assay/Species | Target | Cell Line | IC50 (nM) |
|---|---|---|---|---|
| 340569:308746 | Dose Response/Human | PTEN | 20 | 0.263 |
| 340571:308746 | Dose Response/Human | PTEN | 20 | 3.32 |
| 352820:341401 | Dose Response/Human | PTEN | 20 | 1.0348 |
| 340569:340574 | Dose Response/Human | PTEN | 20 | 0.496 |
| 340571:340573 | Dose Response/Human | PTEN | 20 | 1.36 |
| 352820:352821 | Dose Response/Human | PTEN | 20 | 0.28988 |
| 351827:351828 | RTPCR EIF4E MH-S/Mouse | eIF4E | 243 | 0.054034 |
| 351829:351830 | RTPCR EIF4E MH-S/Mouse | eIF4E | 243 | 0.50058 |
| 351831:351832 | RTPCR EIF4E MH-S/Mouse | eIF4E | 243 | 0.051497 |
| 351833:351834 | RTPCR EIF4E MH-S/Mouse | eIF4E | 243 | 0.092224 |
| 355713:355714 | Dose Response/Human | Survivin | 20 | 0.064756 |
| 355713:355714 | Dose Response/Human | Survivin | 20 | 0.064756 |
| 355713:355714 | Dose Response/Human | Survivin | 20 | 078878 |
| 355713:355714 | Dose Response/Human | Survivin | 160 | 0.107 |
| 355713:355714 | Dose Response/Human | Survivin | 20 | 0.151 |
| 340570:340573 | Dose Response/Human | PTEN | 20 | 1.83 |
| 344219:308746 | Dose Response/Human | PTEN | 20 | 0.886 |

EXAMPLE 31

Effect of Modified Phosphate Moieties on Alternating 2'-O-methyl/2'-F siRNA's Targeting eIF4E A dose response was performed targeting eif4e in HeLa cells to determine the effects of selected terminal groups on activity. More specifically the reduction of eEF4E mRNA in HeLa cells by 19-basepair siRNA containing alternating 2'-OMe/2'-F modifications is shown in this example. HeLa cells (passage 7) were plated at 4000/well and transfected with siRNA in the presence of lipofectin (6 µL/mL opti-MEM) and treated for 4 hours, re-fed, lysed the following day and analized by RT-PCR (RTS96_10). The maximum % reduction is the amount of mRNA reduction compared to untreated control cells at the highest concentration (100 nM), with IC50 indicating the interpolated concentration at which 50% reduction is achieved.

| SEQ ID NO/ ISIS NO | SEQUENCES 5'-3' targeted to eIF4E | |
|---|---|---|
| 14/341401 | 5'-AAGUAAGGACCAGAGACAA-3' | (P=O, sense) |
| 13/341391 | 5'-UUGUCUCUGGUCCUACUU-3' | (P=O, anti-sense) |
| 20/342764 | 5'-AGAGCUAAAGGUGAUAAGA-3' | (P=O, sense) |
| 19/342744 | 5'-UCUUAUCACCUUUAGCUCU-3' | (P=O, anti-sense) |
| 20/351832 | 5'-AGAGCUAAAGGUGAUAAGA-3' | (P=O, sense) |
| 19/351831 | 5'-UCUUAUCACCUUUAGCUCU-3' | (P=O, anti-sense) |
| 20/351832 | 5'-AGAGCUAAAGGUGAUAAGA-3' | (P=O, sense) |
| 19/368681 | 5'-P-UCUUAUCACCUUUAGCUCU-3' | (P=O, anti-sense) |
| 20/351832 | 5'-AGAGCUAAAGGUGAUAAGA-3' | (P=O, sense) |
| 19x/379225 | 5'-P(S)-UCUUAUCACCUUUAGCUCU-3' | (P=O, anti-sense) |
| 20/351832 | 5'-AGAGCUAAAGGUGAUAAGA-3' | (P=O, sense) |
| 19/379712 | 5'-P(H)-UCUUAUCACCUUUAGCUCU-3' | (P=O, anti-sense) |
| 20/351832 | 5'-AGAGCUAAAGGUGAUAAGA-3' | (P=O, sense) |
| 19/379226 | 5'-P(CH₃)-UCUUAUCACCUUUAGCUCU-3' | (P=O, anti-sense) |

Underlined nucleosides are 2'-OCH$_3$ modified nucleosides, bold nucleosides are 2'-F modified nucleosides, 5'-P is 5'-phosphate, 5'-P(S) is a 5'-thiophosphate group (5'-O—P(=S)(OH)OH), 5'-P(H) is a 5'-H-phosphonate group (5'-O—P(=O)(H)OH) and 5'-P(CH$_3$) is a methylphosphonate group (5'-O—P(=O)(CH$_3$)OH). All of the constructs in this assay were full phosphodiester linked as shown in brackets for each construct.

| Double stranded construct | | Activity | |
|---|---|---|---|
| Antisense | Sense | Max Red (100 nM) | IC50 (nM) |
| x/341401 | x/341391 | 103 | n/a (neg control) |
| x/342764 | x/342744 | 11.0 | 1.26 |
| x/351832 | x/351831 | 3.5 | 0.66 |
| x/351832 | x/368681 | 3.6 | 0.14 |
| x/351832 | x/379225 | 2.8 | 0.20 |
| x/351832 | x/379712 | 8.0 | 2.01 |
| x/351832 | x/379226 | 18.1 | 8.24 |

EXAMPLE 32

Effect of Modified Phosphate Moieties on Alternating 2'-O-methyl/2'-F siRNA's Targeting PTEN A dose response was performed targeting PTEN in HeLa cells to determine the effects of selected terminal groups on activity. More specifically the reduction of endogenous PTEN mRNA in HeLa cells by 19-basepair siRNA containing alternating 2'-OMe/2'F modifications was determined. HeLa cells (passage 7) were plated at 4000/well and transfected with siRNA in the presence of lipofectin (6 µL/mL opti-MEM) and treated for 4 hours, re-fed, lysed the following day and analized by RT-PCR (RTS96_10). The maximum % reduction is the amount of MRNA reduction compared to untreated control cells at the highest concentration (100 nM), with IC50 indicating the interpolated concentration at which 50% reduction is achieved.

| SEQ ID NO/ ISIS NO | SEQUENCES 5'-3' targeted to eIF4E | |
|---|---|---|
| 20/342764 | 5'-AGAGCUAAAGGUGAUAAGA-3' | (P=O, sense) |
| 19/342744 | 5'-UCUUAUCACCUUUAGCUCU-3' | (P=O, antisense) |
| 14/341401 | 5'-AAGUAAGGACCAGAGACAA-3' | (P=O, sense) |
| 13/341391 | 5'-UUGUCUCUGGUCCUUACUU-3' | (P=O, antisense) |
| 14/359996 | 5'-AAGUAAGGACCAGAGACAA-3' | (P=O, sense) |
| 13/359995 | 5'-UUGUCUCUGGUCCUUACUU-3' | (P=O, antisense) |
| 14/359996 | 5'-AAGUAAGGACCAGAGACAA-3' | (P=O, sense) |
| 13/352820 | 5'-P-UUGUCUCUGGUCCUUACUU-3' | (P=O, antisense) |
| 14/359996 | 5'-AAGUAAGGACCAGAGACAA-3' | (P=O, sense) |
| 13/377728 | 5'-P(S)-UUGUCUCUGGUCCUUACUU-3' | (P=O, antisense) |
| 14/359996 | 5'-AAGUAAGGACCAGAGACAA-3' | (P=O, sense) |
| 13/377729 | 5'-P(diethyl)-UUGUCUCUGGUCCUUACUU-3' | (P=O, antisense) |
| 14/359996 | 5'-AAGUAAGGACCAGe,uns AGACAA-3' | (P=O, sense) |
| 13/377757 | 5'-P(H)-UUGUCUCUGGUCCUUACUU-3' | (P=O, antisense) |
| 14/359996 | 5'-AAGUAAGGACCe,uns AGAGACAA-3' | (P=O, sense) |
| 13/377759 | 5'-P(CH₃)-UUGUCUCUGGUCCUUACUU-3' | (P=O, antisense) |

Underlined nucleosides are 2'-OCH₃ modified nucleosides, bold nucleosides are 2'-F modified nucleosides, 5'-P is 5'-phosphate, 5'-P(S) is a 5'-thiophosphate group (5'-O-P(=S)(OH)OH), 5'-P(H) is a 5'-H-phosphonate group (5'-O-P(=O)(H)OH), 5'-P(CH₃) is a methylphosphonate group (5'-O-P(=O)(CH₃)OH) and 5'-P(diethyl) is a diethylphosphate group (5'-O-P(=O)(CH₂CH₃)₂).

| Double stranded construct | | Activity | |
|---|---|---|---|
| Antisense | Sense | Max Red (100 nM) | IC50 (nM) |
| x/342764 | x/342744 | 106 | n/a (neg control) |
| x/341401 | x/341391 | 12.2 | 1.14 |
| x/359996 | x/359995 | 14.1 | 4.55 |
| x/359996 | x/352820 | 9.3 | 1.21 |
| x/359996 | x/377728 | 9.4 | 0.90 |
| x/359996 | x/377729 | 97.5 | n/a |
| x/359996 | x/377757 | 19.2 | 5.60 |
| x/359996 | x/377759 | 27.4 | 14.36 |

EXAMPLE 33

Chemically Modified siRNA Targeted to PTEN: in vivo Study

Six- to seven-week old Balb/c mice (Jackson Laboratory, Bar Harbor, Me.) were injected with compounds targeted to PTEN. Each treatment group was comprised of four animals. Animals were dosed via intraperitoneal injection twice per day for 4.5 days, for a total of 9 doses per animal. Saline-injected animals served as negative controls. Animals were sacrificed 6 hours after the last dose of oligonucleotide was administered, and plasma samples and tissues were harvested. Target reduction in liver was also measured at the conclusion of the study.

Two doses of each treatment were tested. Treatment with ISIS 116847 (5'-CTGCTAGCCTCTGGATTTGA-3', SEQ ID NO: 25), a 5-10-5 gapmer was administered at doses of 12.5 mg/kg twice daily or at 6.25 mg/kg twice daily. The siRNA compounds described below were administered at doses of 25 mg/kg twice daily or 6.25 mg/kg twice daily. Each siRNA is composed of an antisense and complement strand as described in previous examples, with the antisense strand targeted to mouse PTEN. ISIS 116847 and all of the siRNAs of this experiment also have perfect complementarity with human PTEN.

An siRNA duplex targeted to PTEN is comprised of antisense strand ISIS 341391 (5'-UUGUCUCUGGUCCUACUU-3', SEQ ID NO: 13) and the sense strand ISIS 341401 (5'-AAGUAAGGACCAGAGACAA-3', SEQ ID NO: 14). Both strands of the ISIS 341391/341401 duplex are comprised of ribonucleosides with phosphodiester internucleoside linkages.

Another siRNA duplex targeted to PTEN is comprised of antisense strand ISIS 359995 (5'-UUGUCUCUGGUCCUACUU-3', SEQ ID NO: 13) and the sense strand ISIS 359996 (5'-AAGUAAGGACCAGAGACAA-3', SEQ ID NO: 14). Both strands of the ISIS 359995/359996 duplex are comprised of alternating 2'-O—CH₃ modified and 2'-F modified nucleosides with a phosphodiester backbone. 2'-F nucleosides are indicated with bold type.

PTEN mRNA levels in liver were measured at the end of the study using real-time PCR and RiboGreen™ RNA quantification reagent (Molecular Probes, Inc. Eugene, Oreg.) as taught in previous examples above. PTEN mRNA levels were determined relative to total RNA (using Ribogreen) or GAPDH expression, prior to normalization to saline-treated control. Results are presented in Table 4 as the average % inhibition of mRNA expression for each treatment group, normalized to saline-injected control.

TABLE 4

Target reduction by chemically modified siRNAs targeted to PTEN in mouse liver

| Treatment | Dose (mg/kg, administered 2x/day) | % Inhibition | |
|---|---|---|---|
| | | Ribogreen | GAPDH |
| ISIS 116847 | 12.5 | 92 | 95 |
| | 6.25 | 92 | 95 |
| ISIS 341391/341401 | 25 | 12 | 21 |
| | 6.25 | 2 | 9 |
| ISIS 359995/359996 | 25 | 6 | 13 |
| | 6.25 | 5 | 13 |

As shown in Table 4, all oligonucleotides targeted to PTEN caused a reduction in mRNA levels in liver as compared to saline-treated control. The mRNA levels measured for the ISIS 341391/341401 duplex are also suggestive of dose-dependent inhibition.

The effects of treatment with the RNA duplexes on plasma glucose levels were evaluated in the mice treated as described above. Approximate average plasma glucose is presented in Table 5 for each treatment group.

TABLE 5

Effects of chemically modified siRNAs targeted to PTEN on plasma glucose levels in normal mice

| Treatment | Dose (mg/kg, administered 2x/day) | Plasma glucose (mg/dL) |
|---|---|---|
| Saline | N/A | 186 |
| ISIS 116847 | 12.5 | 169 |
| | 6.25 | 166 |
| ISIS 341391/341401 | 25 | 159 |
| | 6.25 | 182 |
| ISIS 359996/359995 | 25 | 182 |
| | 6.25 | 169 |

To assess the physiological effects resulting from in vivo siRNA targeted to PTEN mRNA, the mice were evaluated at the end of the treatment period for plasma triglycerides, plasma cholesterol, and plasma transaminase levels. Plasma cholesterol levels from animals treated with either dose of ISIS 116847 were increased about 20% over levels measured for saline-treated animals. Conversely, the cholesterol levels measured for animals treated with either the 25 mg/kg or the 6.25 mg/kg doses of the ISIS 341391/341401 duplex were decreased about 12% as compared to saline-treated controls. The ISIS 359996/359995 duplex did not cause significant alterations in cholesterol levels. All of the treatment groups showed decreased plasma triglycerides as compared to saline-treated control, regardless of treatment dose.

Increases in the transaminases ALT and AST can indicate hepatotoxicity. The transaminase levels measured for mice treated with the siRNA duplexes were not elevated to a level indicative of hepatotoxicity with respect to saline treated control. Treatment with 12.5 mg/kg doses of ISIS 116847 caused approximately 7-fold and 3-fold increases in ALT and AST levels, respectively. Treatment with the lower doses (6.25 mg/kg) of ISIS 116847 caused approximately 4-fold and 2-fold increases in ALT and AST levels, respectively.

At the end of the study, liver, white adipose tissue (WAT), spleen, and kidney were harvested from animals treated with the oligomeric compounds and were weighed to assess gross organ alterations. Approximate average tissue weights for each treatment group are presented in Table 6.

TABLE 6

Effects of chemically modified siRNAs targeted to PTEN on tissue weight in normal mice

| Treatment | Dose (mg/kg, administered 2x/day) | Liver | WAT | Spleen | Kidney |
|---|---|---|---|---|---|
| | | | Tissue weight (g) | | |
| Saline | N/A | 1.0 | 0.5 | 0.1 | 0.3 |
| ISIS 116847 | 12.5 | 1.1 | 0.4 | 0.1 | 0.3 |
| | 6.25 | 1.1 | 0.4 | 0.1 | 0.3 |
| ISIS 341391/341401 | 25 | 1.0 | 0.3 | 0.1 | 0.3 |
| | 6.25 | 0.9 | 0.4 | 0.1 | 0.3 |
| ISIS 359996/359995 | 25 | 1.1 | 0.4 | 0.1 | 0.3 |
| | 6.25 | 1.0 | 0.3 | 0.1 | 0.4 |

As shown in Table 6, treatment with antisense oligonucleotides or siRNA duplexes targeted to PTEN did not substantially alter liver, WAT, spleen, or kidney weights in normal mice as compared to the organ weights of mice treated with saline alone.

EXAMPLE 34

Stability of Alternating 2'-O-methyl/2'-fluoro siRNA Constructs in Mouse Plasma

Intact duplex RNA was analyzed from diluted mouse-plasma using an extraction and capillary electrophoresis method similar to those previously described (Leeds, J. M., et al., 1996, *Anal. Biochem.*, 235, 3643; Geary, R. S., et al., 1999, *Anal. Biochem.*, 274, 241-248. Heparin-treated mouse plasma, from 3-6 month old female Balb/c mice (Charles River Labs) was thawed from −80° C. and diluted to 25% (v/v) with phosphate buffered saline (140 mM NaCl, 3 mM KCl, 2 mM potassium phosphate, 10 mM sodium phosphate). Approximately 10 nmol of pre-annealed siRNA, at a concentration of 100 µM, was added to the 25% plasma and incubated at 37° C. for 0, 15, 30, 45, 60, 120, 180, 240, 360, and 420 minutes. Aliquots were removed at the indicated time, treated with EDTA to a final concentration of 2 mM, and placed on ice at 0° C. until analyzed by capillary gel electrophoresis (Beckman P/ACE MDQ-UV with eCap DNA Capillary tube). The area of the siRNA duplex peak was measured and used to calculate the percent of intact siRNA remaining. Adenosine triphosphate (ATP) was added at a concentration of 2.5 mM to each injection as an internal calibration standard. A zero time point was taken by diluting siRNA in phosphate buffered saline followed by capillary electrophoresis. Percent intact siRNA was plotted against time, allowing the calculation of a pseudo first-order half-life. Results are shown in Table 7.

TABLE 7

Stability of alternating 2'-O-methyl/2'-fluoro siRNA constructs in mouse plasma

| Construct | Time (minutes) | | | | | | | | |
|---|---|---|---|---|---|---|---|---|---|
| | 0 | 15 | 30 | 45 | 60 | 120 | 180 | 240 | 360 |
| 338918_338943 | 76.98 | 71.33 | 49.77 | 40.85 | 27.86 | 22.53 | 14.86 | 4.18 | 0 |
| 351831_351832 | 82.42 | 81.05 | 79.56 | 77.64 | 75.54 | 75.55 | 75.56 | 75.55 | 75 |

The parent (unmodified) construct is approximately 50% degraded after 30 minutes and nearly gone after 4 hours (completely gone at 6 hours). In contrast, the alternating 2'-O-methyl/2'-fluoro construct remains relatively unchanged and 75% remains even after 6 hours.

EXAMPLE 35

In Vivo Inhibition of Survivin Expression in a Human Glioblastoma Xenograft Tumor Model The U-87MG human glioblastoma xenograft tumor model (Kiaris H, Schally A V, Varga J L, 2000 May-Jun; 2(3):242-50) was used to demonstrate the antitumor activity of selected compositions of the present invention. A total of 8 CD1 nu/nu (Charles River) mice were used for each group. For implantation, tumor cells were trypsinized, washed in PBS and resuspended in PBS at 4×10⁶ cells/mL in DMEM. Just before implantation, animals were irradiated (450 TBI) and the cells were mixed in Matrigel (1:1). A total of 4×10⁶ tumor cells in a 0.2 mL volume were injected subcutaneously (s.c.) in the left rear flank of each mouse. Treatment with the selected double stranded compositions (dissolved in 0.9% NaCl, injection grade), or vehicle (0.9% NaCl) was started 4 days post tumor cell implantation. The compositions were administered intravenously (i.v.) in a 0.2 mL volume eight hours apart on day one and four hours apart on day two. Tissues (tumor, liver, kidney, serum) were collected two hours after the last dose. Tumors from eight animals from each group were homogenized for western evaluation. Survivin levels were determined and compared to saline controls.

The alternating 2'-OCH₃/2'-F composition shown below was evaluated in the human glioblastoma xenograft tumor model to determine in vivo inhibition survivin gene expression. A composition comprising two 19 mer oligomeric compounds wherein both oligomeric compounds are fully alternating 2'-OCH₃/2'-F having an offset register with the 5'-end of the antisense having a 2'-OCH₃ modified nucleoside. Underlined nucleosides are 2'-OCH₃ modified nucleosides and bold are 2'-F modified nucleosides.

| SEQ ID No/ISIS No | Sequence 5'-3' | |
|---|---|---|
| 24/355714 | GGAGAUCAACAUUUUCAAA | (S, PO) |
| 23/355713 | UUUGAAAAUGUUGAUCUCC | (AS, PO) |

Treatment with this construct resulted in 60% inhibition of Survivin production as compared with tumor bearing animals treated with a saline control. These data demonstrate that siRNA having alternating motifs in both strands are effective at reducing gene expression in vivo.

While the present invention has been described with specificity in accordance with certain of its preferred embodiments, the following examples serve only to illustrate the invention and are not intended to limit the same.

What is claimed:

1. A method of reducing target messenger RNA in a cell comprising contacting the cell with a composition comprising first and second chemically synthesized oligomeric compounds, wherein:
   the first oligomeric compound is complementary to and capable of hybridizing to the second oligomeric compound and to the target messenger RNA;
   each of the first and second oligomeric compounds independently comprises from 17 to 23 nucleosides;
   the first oligomeric compound comprises a contiguous sequence of linked nucleosides that define an alternating motif of the formula:

$5'-Q(-L-Z-L-Q)_n(-L-Z)_{nn}-3'$;

wherein:
   each L is an internucleoside linking group;
   either each Q is a 2'F-nucleoside and each Z is a 2'OMe-nucleoside; or each Q is a 2'OMe-nucleoside and each Z is a 2'F-nucleoside; and
   n is from 8 to 14 and nn is 0 or 1;
   thereby reducing the target messenger RNA in the cell.

2. The method of claim 1 wherein said first oligomeric compound further comprises a 5'-phosphate group.

3. The method of claim 1 wherein said second oligomeric compound further comprises a 5'-phosphate group.

4. The method of claim 1 wherein each of said first and said second oligomeric compounds independently, comprise a 5'-phosphate group.

5. The method of claim 1 wherein said first oligomeric compound comprises a 3'-terminal OH group.

6. The method of claim 1 wherein each internucleoside linking group (L) is a phosphodiester internucleoside linking group.

7. The method of claim 1 wherein each internucleoside linking group (L) is a phosphorothioate internucleoside linking group.

8. The method of claim 1 wherein each internucleoside linking group (L) of one of said first and said second oligomeric compounds is a phosphorothioate internucleoside linking group and each internucleoside linking group of the other of said first and said second oligomeric compounds is a phosphodiester internucleoside linking group.

9. The method of claim 1 wherein each internucleoside linking group (L) of said first oligomeric compound is a phosphorothioate internucleoside linking group and each internucleoside linking group of said second oligomeric compound is a phosphodiester internucleoside linking group.

10. The method of claim 1 wherein each internucleoside linking group (L) of said first and said second oligomeric compounds is independently a phosphorothioate or phosphodiester internucleoside linking group.

11. The method of claim 1 wherein each of the internucleoside linking groups (L) of said first and said second oligomeric compounds is independently selected from the group consisting of phosphodiester, phosphorothioate, chiral phosphorothioate, phosphorodithioate, phosphotriester, aminoalkylphosphotriester, methyl phosphonate, alkyl phosphonate, 5'-alkylene phosphonate, chiral phosphonate, phosphinate, phosphoramidate, 3'-amino phosphoramidate, aminoalkylphosphoramidate, thionophosphoramidate, thionoalkylphosphonate, thionoalkylphosphotriester, selenophosphate and boranophosphate.

12. The method of claim 1 further comprising at least one conjugate group.

13. The method of claim 1 wherein at least one of said first and said second oligomeric compounds further comprises at least one conjugate group attached at the 3'-end or the 5'-end or one conjugate group attached at the 3'-end and a second conjugate group attached at the 5'-end.

14. The method of claim 1 wherein at least one of said first and said second oligomeric compounds further comprises at least one terminal cap moiety attached at the 3'-end or the 5'-end or one terminal cap moiety attached at the 3'-end and a second terminal cap moiety attached at the 5'-end.

15. The method of claim 14 wherein each of said terminal cap moieties is an inverted deoxy abasic moiety.

16. The method of claim 14 wherein said second oligomeric compound is a sense strand comprising a terminal cap moiety at 3'-end, the 5'-end or one terminal cap at the 3'-end and a second terminal cap at the 5'-end.

17. The method of claim 16 wherein said terminal cap moiety is an inverted deoxy abasic moiety.

18. The method of claim 1 wherein said first and said second oligomeric compounds are a complementary pair of siRNA oligonucleotides.

19. The method of claim 1 wherein said first and said second oligomeric compounds are an antisense/sense pair of oligonucleotides.

20. The method of claim 1 wherein said first oligomeric compound is an antisense oligonucleotide.

21. The method of claim 1 wherein said second oligomeric compound is a sense oligonucleotide.

* * * * *